US009079851B2

(12) United States Patent
Gadewar et al.

(10) Patent No.: US 9,079,851 B2
(45) Date of Patent: *Jul. 14, 2015

(54) ETHYL ACETATE PRODUCTION

(75) Inventors: Sagar B. Gadewar, Goleta, CA (US); Brian Christopher Vicente, Santa Barbara, CA (US); Robert Elliot Norton, Montecito, CA (US); Michael Francis Doherty, Santa Barbara, CA (US)

(73) Assignee: Greenyug, LLC, Santa Barbara, CA (US)

( * ) Notice: Subject to any disclaimer, the term of this patent is extended or adjusted under 35 U.S.C. 154(b) by 835 days.

This patent is subject to a terminal disclaimer.

(21) Appl. No.: 13/363,858

(22) Filed: Feb. 1, 2012

(65) Prior Publication Data
US 2013/0197266 A1    Aug. 1, 2013

(51) Int. Cl.
| C07C 67/40 | (2006.01) |
| C07C 67/54 | (2006.01) |
| C07C 67/60 | (2006.01) |
| C07C 67/00 | (2006.01) |

(52) U.S. Cl.
CPC .................. *C07C 67/40* (2013.01); *C07C 67/00* (2013.01); *C07C 67/54* (2013.01); *C07C 67/60* (2013.01)

(58) Field of Classification Search
CPC ....................................................... C07C 67/40
USPC ......................................................... 560/239
See application file for complete search history.

(56) References Cited

U.S. PATENT DOCUMENTS

| 1,992,480 | A | 2/1935 | Fuchs et al. |
| 2,525,829 | A | 10/1950 | Royer et al. |
| 3,714,236 | A | 1/1973 | Wright, Jr. et al. |
| 4,052,424 | A | 10/1977 | Vanderspurt |
| 4,220,803 | A | 9/1980 | Marcinkowsky et al. |
| 4,379,028 | A | 4/1983 | Berg et al. |
| 4,435,595 | A | 3/1984 | Agreda et al. |
| 4,440,946 | A | 4/1984 | Summerville et al. |
| 4,523,027 | A | 6/1985 | Kummer et al. |

(Continued)

FOREIGN PATENT DOCUMENTS

| BR | 9104652 A | 4/1993 |
| EP | 0101910 A1 | 3/1984 |

(Continued)

OTHER PUBLICATIONS

Filing receipt and specification for patent application entitled "Ethyl acetate production," by Sagar B. Gadewar, et al., filed Sep. 10, 2013 as U.S. Appl. No. 14/023,125.

(Continued)

*Primary Examiner* — Joseph Kosack
*Assistant Examiner* — Matthew Coughlin
(74) *Attorney, Agent, or Firm* — Conley Rose, P.C.; Rodney B. Carroll

(57) ABSTRACT

A reactive distillation method comprises introducing an feed stream comprising ethanol to a reactive distillation column, contacting the feed stream with a catalyst in the reactive distillation column during a distillation, where the feed stream reacts in the presence of the catalyst to produce a reaction product comprising ethyl acetate and hydrogen, removing ethyl acetate during the distillation from the reactive distillation column as a bottoms stream, and removing hydrogen during the distillation from the reactive distillation column as an overhead stream.

38 Claims, 11 Drawing Sheets

(56) References Cited

U.S. PATENT DOCUMENTS

| | | | |
|---|---|---|---|
| 4,569,726 A | 2/1986 | Berg et al. | |
| 4,645,570 A | 2/1987 | Sridhar et al. | |
| 4,825,013 A | 4/1989 | Quarderer et al. | |
| 4,996,007 A | 2/1991 | Chao et al. | |
| 5,194,675 A | 3/1993 | Joerg et al. | |
| 5,334,751 A | 8/1994 | Lemanski et al. | |
| 6,407,295 B1 | 6/2002 | Kaizik et al. | |
| 6,632,330 B1 | 10/2003 | Colley et al. | |
| 6,809,217 B1* | 10/2004 | Colley et al. | 560/231 |
| 7,700,810 B2 | 4/2010 | Kourtakis et al. | |
| 7,700,811 B2 | 4/2010 | Kourtakis et al. | |
| 7,700,812 B2 | 4/2010 | Kourtakis et al. | |
| 7,700,813 B2 | 4/2010 | Kourtakis et al. | |
| 7,705,192 B2 | 4/2010 | Kourtakis et al. | |
| 7,745,672 B2 | 6/2010 | Kourtakis et al. | |
| 8,071,823 B2 | 12/2011 | Ozer et al. | |
| 8,080,684 B2 | 12/2011 | Hassan et al. | |
| 8,080,695 B2 | 12/2011 | Tsuchida et al. | |
| 8,304,587 B2 | 11/2012 | Warner et al. | |
| 8,318,989 B2 | 11/2012 | Kourtakis et al. | |
| 2012/0035390 A1* | 2/2012 | Gadewar | 560/239 |
| 2012/0178962 A1 | 7/2012 | Gadewar | |

FOREIGN PATENT DOCUMENTS

| | | |
|---|---|---|
| EP | 0151886 A1 | 8/1985 |
| EP | 0201105 A1 | 11/1986 |
| EP | 0331021 A1 | 9/1989 |
| FR | 2743060 A1 | 7/1997 |
| GB | 287846 | 4/1929 |
| GB | 312345 | 8/1930 |
| GB | 470773 | 8/1937 |
| JP | 59025334 A | 2/1984 |
| JP | 5186392 A | 7/1993 |
| JP | 7053676 B2 | 6/1995 |
| SU | 362814 A1 | 12/1972 |
| WO | 2011131609 A2 | 10/2011 |
| WO | 2013055334 A1 | 4/2013 |
| WO | 2013116492 A1 | 8/2013 |

OTHER PUBLICATIONS

Foreign communication from a related counterpart application—International Search Report and Written Opinion, PCT/US2013/024104, May 30, 2013, 12 pages.

Inui, Kanichiro, et al., "Direct synthesis of ethyl acetate from ethanol carried out under pressure," Journal of Catalysis, 2002, pp. 207-215, vol. 212, Elsevier Science.

Machine translation (9 pages) of French patent No. 2743060 A1 issued on Jul. 4, 1997.

Santacesaria, E., et al., "Ethanol dehydrogenation to ethyl acetate by using copper and copper chromite catalysts," Chemical Engineering Journal, 2012, pp. 209-220, vol. 179, Elsevier B.V.

Smith, Michael B., "March's advanced organic chemistry: reactions, mechanisms, and structure," 7th edition, 2013, 8 pages of cover, publishing information, and contents, John Wiley & Sons, Inc.

Vogel, Arthur Israel, "Vogel's textbook of practical organic chemistry," 5th edition, revised by Brian S. Furniss, et al., 1989, 15 pages of cover, publishing information, and contents, John Wiley & Sons, Inc.

Filing receipt and specification for patent application entitled "Production of higher alcohols," by Sagar B. Gadewar, et al., filed Feb. 18, 2014 as U.S. Appl. No. 14/183,273.

Filing receipt and specification for provisional patent application entitled "Production of butanols and ethyl acetate," by Sagar B. Gadewar, et al., filed Feb. 19, 2013 as U.S. Appl. No. 61/766,484.

Filing receipt and specification for provisional patent application entitled "Production of higher alcohols from ethanol," by Brian Christopher Vicente, et al., filed Dec. 5, 2013 as U.S. Appl. No. 61/912,235.

Yang, Ke Wu, et al., "One-step Synthesis of n-Butanol from Ethanol Condensation over Alumina-supported Metal Catalysts," Chinese Chemical Letters, 2004, pp. 1497-1500, vol. 15, No. 12.

Filing receipt and specification for provisional patent application entitled "Production of ethyl acetate and butyl acetates from ethanol," by Sagar B. Gadewar, et al., filed Dec. 4, 2013 as U.S. Appl. No. 61/911,832.

Filing receipt and specification for international application entitled "Production of higher alcohols," filed Feb. 18, 2014 as international application No. PCT/US2014/016957.

Filing receipt and specification for international application entitled "Ethyl acetate production," filed Oct. 20, 2010 as international application No. PCT/US2010/002806.

Foreign communication from a related counterpart application—International Preliminary Report on Patentability, PCT/US2011/056015, Apr. 15, 2014, 6 pages.

Foreign communication from a related counterpart application—International Search Report and Written Opinion, PCT/US2013/024104, May 30, 2013, 14 pages.

Inui, Kanichiro, et al., "Direct Synthesis of Ethyl Acetate from Ethanol Carried Out under Pressure," Journal of Catalysis: 2004, pp. 207-215, vol. 212, Elsevier B.V.

Notice of Allowance dated May 24, 2013 (11 pages), U.S. Appl. No. 12/925,460, filed Oct. 20, 2010.

Notice of Allowance dated Jun. 4, 2013 (8 pages), U.S. Appl. No. 13/422,743, filed Mar. 16, 2012.

Office Action (Restriction Requirement) dated Oct. 15, 2012 (6 pages), U.S. Appl. No. 13/422,743, filed Mar. 16, 2012.

Office Action (Restriction Requirement) dated Nov. 5, 2012 (7 pages), U.S. Appl. No. 12/925,460, filed Oct. 20, 2010.

Office Action dated Jan. 10, 2013 (10 pages), U.S. Appl. No. 13/422,743, filed Mar. 16, 2012.

Office Action dated Feb. 4, 2013 (13 pages), U.S. Appl. No. 12/925,460, filed Oct. 20, 2010.

Office Action dated Apr. 18, 2013 (14 pages), U.S. Appl. No. 12/925,460, filed Oct. 20, 2010.

Foreign communication from a related counterpart application—International Search Report and Written Opinion, PCT/US2014/016957, Jun. 27, 2014, 9 pages.

Foreign communication from a related counterpart application—International Preliminary Report on Patentability, PCT/US2013/024104, Aug. 5, 2014, 9 pages.

Foreign communication from a related counterpart application—International Search Report and Written Opinion, PCT/US2014/053894, Oct. 31, 2014, 9 pages.

Office Action dated Oct. 27, 2014 (17 pages), U.S. Appl. No. 14/183,273, filed Feb. 18, 2014.

Filing receipt and specification for provisional patent application entitled "Ethyl acetate production," by Sagar B. Gadewar, filed Oct. 20, 2009 as U.S. Appl. No. 61/253,349.

Foreign communication from a related counterpart application—International Search Report and Written Opinion, PCT/US2011/056015, May 24, 2012, 8 pages.

Inui, Kanichiro, et al., "Effective formation of ethyl acetate from ethanol over Cu—Zn—Zr—Al—O catalyst," Journal of Molecular Catalysis A: Chemical, 2004, pp. 147-156, vol. 216, Elsevier B.V.

Takeshita, Kenji, et al., "Reduced copper catalyzed conversion of primary alcohols into esters and ketones," Bulletin of the Chemical Society of Japan, 1978, pp. 2622-2627, vol. 51, No. 9.

Tsai, Reui-Chiang, et al., "Design and control of the side reactor configuration for production of ethyl acetate," Ind. Eng. Chem. Res., 2008, pp. 9472-9484, vol. 47, No. 23, American Chemical Society.

* cited by examiner

Figure 1: Reactive residue curve maps at pressures of 1 atm and 5 atm.

Figure 2: Reactive residue curve maps at pressures of 10 atm and 20 atm.

Figure 3: Single feed reactive distillation column schematic.

Figure 4: Schematic for a reactive distillation system with subsequent product hydrogenation.

Figure 5: Double feed reactive distillation column schematic with an upper feed of ethanol and lower feed of hydrogen.

Figure 6: Double feed reactive distillation column schematic using dual catalyst beds with an upper feed of ethanol and lower feed of hydrogen.

Figure 7: Side reactor configuration (a) upward flow feed to side reactor (b) downward flow feed to side reactor.

Figure 8: Double Side reactor configuration (a) upward flow feed to multiple side reactors (b) downward flow feed to multiple side reactors.

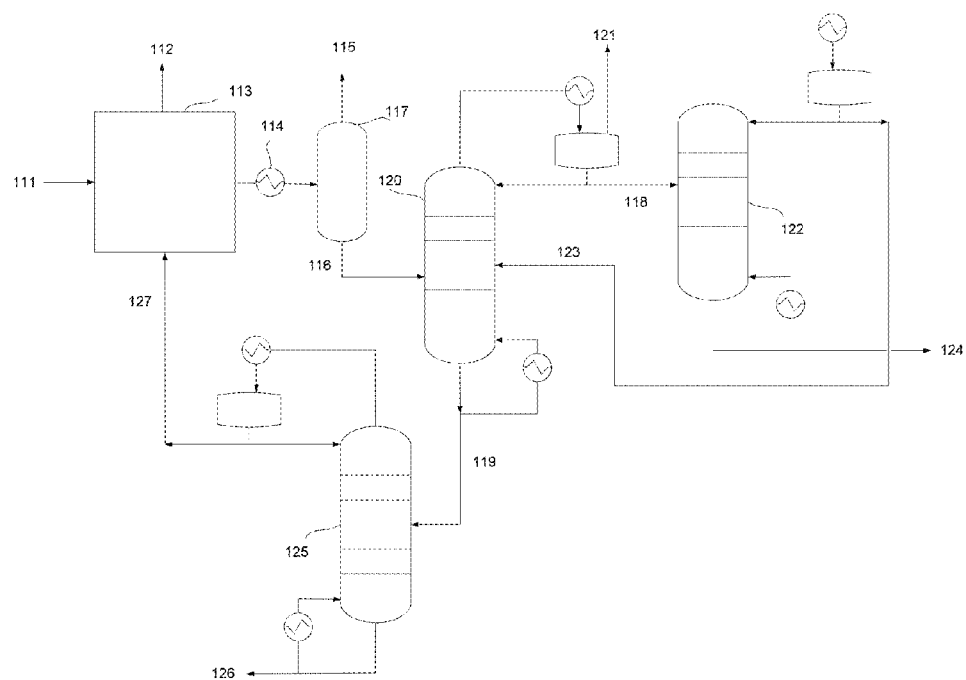
Figure 10: Process configuration for product purification and ethanol recycle.

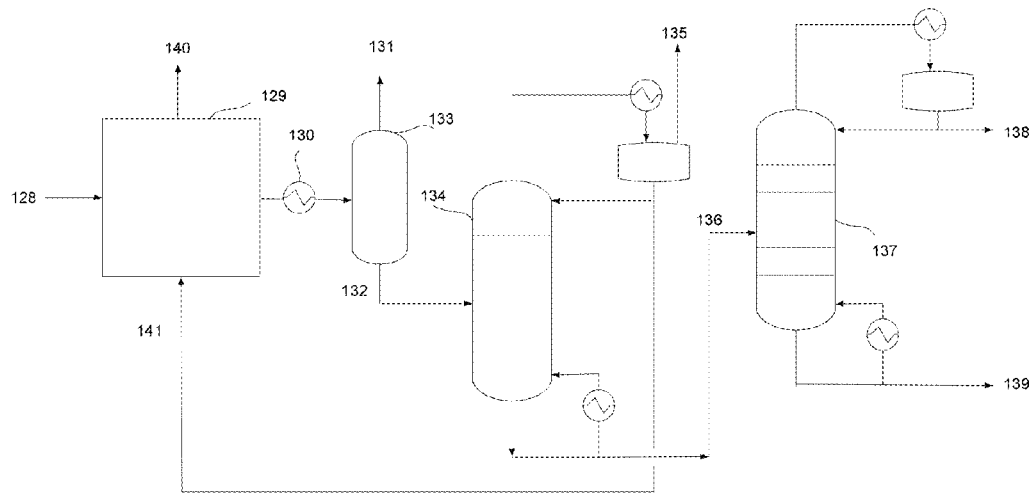
Figure 11: Indirect separation sequence for product purification and ethanol recycle.

ETHYL ACETATE PRODUCTION

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Ethyl acetate can be produced from several different reactions. The most common method for making ethyl acetate is the esterification of acetic acid and ethanol. This reaction requires two raw material supplies with the associated storage or production facilities. In locations without a sufficient supply of reliable, inexpensive acetic acid, this process may not be economically viable.

Ethyl acetate can also be produced from the oxidation of ethanol over supported precious metal catalysts. The high costs of precious metal catalyst can also make this option uneconomical. In addition, the oxidation of ethanol results in the presence of water in the product stream, which can result in a relatively expensive separation system to purify the product.

The Tishchenko reaction (dimerization of aldehydes into esters) is another alternative process for production of ethyl acetate. Dimerization of acetaldehyde results in ethyl acetate, however, aldol condensation also occurs, resulting in by-products such as 2-butnaone and 2-propanol, both of which form azeotropes with ethyl acetate. In addition, the Tishchenko reaction requires a supply of acetaldehyde, which may not be readily available and can be difficult to store and handle due to its high toxicity.

SUMMARY

In an embodiment, a reactive distillation method comprises introducing an feed stream to a reactive distillation column, wherein the feed stream comprises ethanol, contacting the feed stream with a catalyst in the reactive distillation column during a distillation, wherein the feed stream reacts in the presence of the catalyst to produce a reaction product comprising ethyl acetate and hydrogen, removing ethyl acetate during the distillation from the reactive distillation column as a bottoms stream, and removing hydrogen during the distillation from the reactive distillation column as an overhead stream. The method may also include contacting the bottoms stream with a hydrogenation catalyst and hydrogen to hydrogenate at least a portion of a contaminant in the bottoms stream, and separating the hydrogenated portion of the contaminant from the bottoms stream. The hydrogenation catalyst may comprise a Group VIII metal, a Group VI metal, or any combination thereof. The catalyst may comprise at least one catalytic component selected from the group consisting of: copper, copper oxide, barium, barium oxide, ruthenium, ruthenium oxide, rhodium, rhodium oxide, platinum, platinum oxide, palladium, palladium oxide, rhenium, rhenium oxide, silver, silver oxide, cadmium, cadmium oxide, zinc, zinc oxide, zirconium, zirconium oxide, gold, gold oxide, thallium, thallium oxide, magnesium, magnesium oxide, manganese, manganese oxide, aluminum, aluminum oxide, chromium, chromium oxide, nickel, nickel oxide, iron, iron oxide, molybdenum, molybdenum oxide, sodium, sodium oxide, sodium carbonate, strontium, strontium oxide, tin, tin oxide, and any mixture thereof. The catalyst may comprise a support, wherein the support comprises at least one support material selected from the group consisting of: carbon, silica, silica-alumina, alumina, zirconia, titania, ceria, vanadia, nitride, boron nitride, heteropolyacids, hydroxyapatite, zinc oxide, chromia, a zeolite, a carbon nanotube, carbon fullerene, and any combination thereof. The catalyst may comprise copper, and the catalyst may have a copper weight loading of between about 0.5% and about 80% of the catalyst.

The catalyst may comprise copper oxide and zinc oxide disposed on a support; copper oxide, zinc oxide, zirconium oxide, and alumina; and/or copper oxide, zinc oxide, zirconium oxide, and chromium oxide. The catalyst may comprise an alkaline earth metal or alkaline earth metal oxide, copper or copper oxide, and a support. The catalyst may comprise sodium carbonate, and/or the catalyst may be at least partially reduced in the presence of hydrogen. A conversion of ethanol in the feed stream may be at least about 10%, and/or a selectivity of the conversion of ethanol to ethyl acetate may be at least about 60%. The method may also include removing a side stream from the reactive distillation column, and contacting the side stream with a second catalyst, wherein the side stream reacts in the presence of the second catalyst to produce ethyl acetate. A liquid portion of the feed stream may react in the presence of the catalyst to produce a reaction product comprising ethyl acetate and hydrogen.

In an embodiment, a reactive distillation system comprises a reactive distillation column comprising: a dehydrogenation catalyst located generally centrally in the column, an ethanol feed in fluid communication with the reactive distillation column and configured to pass ethanol over the dehydrogenation catalyst, an overhead product hydrogen removal passage, and a bottoms product ethyl acetate removal passage. The reactive distillation system also comprises a product separation system comprising an inlet configured to receive the bottoms product from the reactive distillation column, an ethyl acetate product removal passage, and an ethanol removal passage; and a recycle line coupling the ethanol removal passage from the product separation system and an inlet to the reactive distillation column. The system may also include a hydrogenation catalyst positioned to contact a liquid product following passage over the dehydrogenation catalyst. The product separation system may also include at least one of a lights product removal passage or a heavies product removal passage. 20. The reactive distillation column may comprise a batch reactor configured to contact a liquid ethanol feed with the dehydrogenation catalyst and remove hydrogen during the contacting of the liquid ethanol feed with the dehydrogenation catalyst.

In an embodiment, a reactive distillation method comprises introducing an feed stream to a reactive distillation column, wherein the feed stream comprises ethanol; contacting the feed stream with a catalyst in the reactive distillation column during a distillation, wherein the feed stream reacts in the presence of the catalyst to produce a reaction product comprising ethyl acetate and hydrogen; separating bottoms stream during the distillation from the reactive distillation column, wherein the bottoms stream comprises ethyl acetate and ethanol; separating a recycle stream from the bottoms stream, wherein the recycle stream comprises at least a portion of the ethanol from the bottoms stream; and recycling the recycle stream to the reactive distillation column. The method may also include separating the bottoms stream into an overhead stream and the recycle stream at a first pressure, where the overhead stream comprises ethanol and ethyl acetate; and separating the overhead stream into an ethanol stream and an ethyl acetate product stream at a second pressure, where the second pressure is greater than the first pressure. The method may also include combining the ethanol stream with the bottoms stream in the separation of the bottoms stream into the overhead stream and the recycle stream. The method may also include separating at least one byproduct from the recycle stream after separation of the recycle stream from the bottoms stream and prior to recycling the recycle stream to the reactive distillation column. The method may also include separating the bottoms stream into a product stream and the recycle stream; and separating the product stream into a byproduct stream and an ethyl acetate product stream These and other features will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description.

FIG. 10 illustrates a schematic flow diagram of a product separation system according to an embodiment.

FIG. 11 illustrates a schematic flow diagram of a product separation system according to another embodiment.

DETAILED DESCRIPTION

Figure 1:
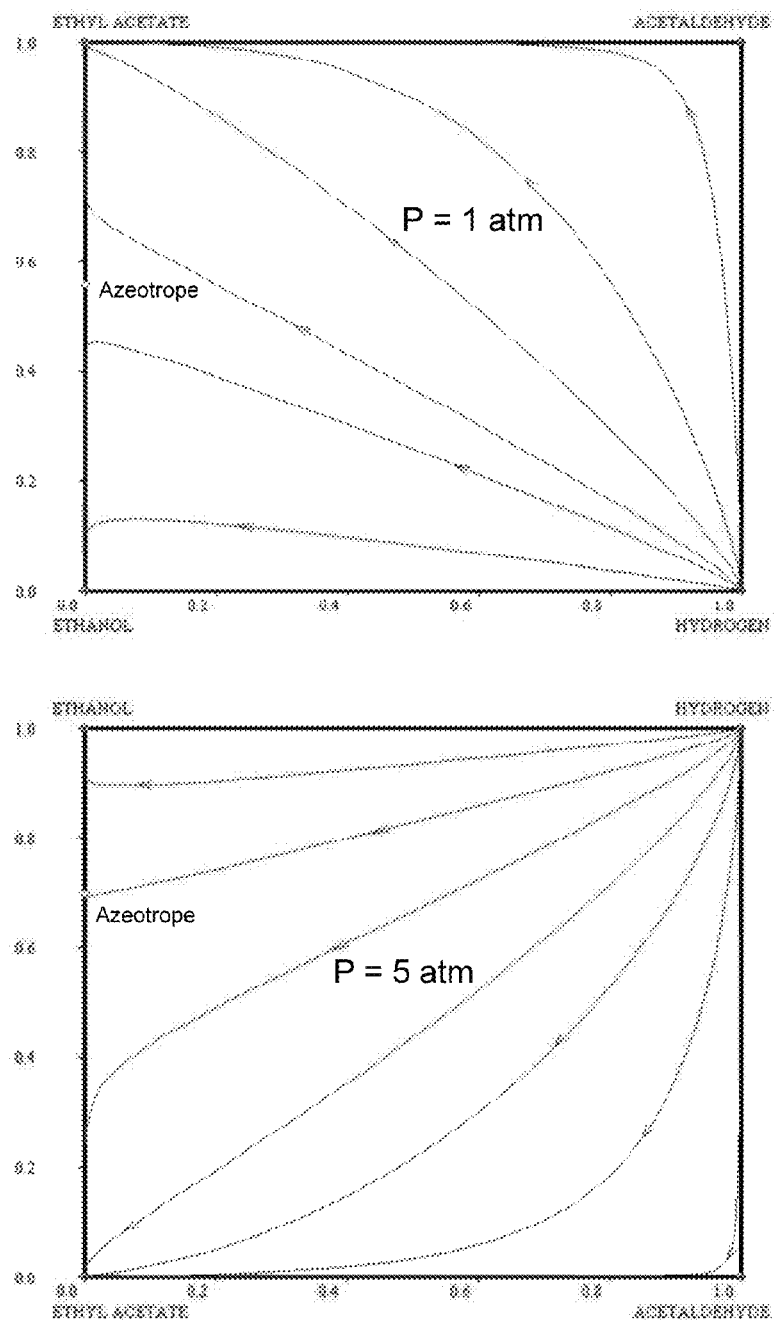
FIG. 1 shows reactive residue maps for conversion of ethanol to ethyl acetate at pressures of 1 and 5 atmospheres (atm) for an embodiment.

A reactive distillation system and process are disclosed herein for producing high purity ethyl acetate from ethanol. This process is beneficial as it provides an improved commercial method of upgrading ethanol to ethyl acetate, a more valuable product. This improved commercial process may be used where there is a supply and/or a surplus supply of ethanol. Further, this process reduces and/or eliminates the need for a separate acetaldehyde or acetic acid plant to provide the precursors for the ethyl acetate production process. The raw material may comprise only ethanol, which may present an advantage relative to other processes requiring multiple feedstocks. In addition, bio-derived ethanol may be used to allow the process to be operated from renewable ethanol sources. Further, the present system and method may utilize base-metal catalysts, which may be less expensive than the precious metal based catalysts of other ethyl acetate production routes. Such catalysts can comprise copper, and may be composed of copper oxide mixed with one or more additional metals and/or metal oxides. The present systems and methods may allow for a one-step ethyl acetate production process, which may be advantageous relative to other processes that require further steps to purify the ethyl acetate product, including a selective removal of 2-butnaone, which forms a low boiling azeotrope with ethyl acetate. Each of these advantages may be provided in a process that can also be less expensive than alternative processes by ethyl acetate production from ethanol.

In an embodiment, the present systems and methods can provide a route to ethyl acetate by dehydrogenation and dimerization of ethanol which is capable of yielding high purity ethyl acetate from ethanol feed streams containing significant amounts of impurities. One issue in the production of ethyl acetate by dehydrogenation of ethanol is that the reaction product mixture is commonly a complex mixture including esters, alcohols, aldehydes and ketones. From a distillative separation point of view, the mixture is further complicated due to the presence of azeotropes. The reaction product mixtures commonly contain components with boiling points close to ethyl acetate (such as n-butyraldehyde and/or butan-2-one), including components which can form azeotropes with ethyl acetate, and/or other components of the mixture. This may present a challenge when high purity ethyl acetate is desired.

In chemical processing, chemical reaction and the purification of the desired products by distillation may be carried out sequentially. The performance of this chemical process structure may be improved by the integration of reaction and distillation in a single multifunctional process unit. This integration concept is called "reactive distillation." As advantages of this integration, chemical equilibrium limitations may be overcome, higher selectivities may be achieved, the heat of reaction may be used in situ for distillation, auxiliary solvents may be avoided, and/or azeotropic and/or closely boiling mixtures may be more easily separated. Increased process efficiency and reduction in overall capital costs may result from the use of this approach.

A reactive distillation system comprises at least one separator (e.g., a distillation tower) in which a reaction is occurring. In general, suitable separators may include any process equipment suitable for separating at least one inlet stream into a plurality of effluent streams having different compositions, states, temperatures, and/or pressures. For example, the separator may be a column having trays, packing, or some other type of complex internal structure. Examples of such columns include scrubbers, strippers, absorbers, adsorbers, packed columns, and distillation columns having valve, sieve, or other types of trays. Such columns may employ weirs, downspouts, internal baffles, temperature control elements, and/or pressure control elements. Such columns may also employ some combination of reflux condensers and/or reboilers, including intermediate stage condensers and reboilers. In an embodiment, the reactive distillation system described herein may comprise a distillation tower having at least one catalyst disposed therein.

As indicated above, the present systems and methods provide for the production of ethyl acetate from ethanol at a relatively low cost, along with a plant or distillation system with significantly reduced complexity using reactive distillation. The present disclosure further provides an improved process for the production of high purity ethyl acetate from ethanol, or from a feedstock comprising a major proportion of ethanol and a minor proportion of impurities such as iso-propanol and iso-butanol. While not commonly present in ethanol feed streams, impurities that can poison the particular catalyst used should be limited, avoided and/or removed. For example, sulfur or nitrogen heterocyclic compounds can frequently act as catalyst poisons and, if present, should be removed before introducing the ethanol feed stream to the reactive distillation column. In an embodiment, the ethanol feed may comprise water. The presence of water in the ethanol feed does not severely reduce the performance of the catalysts, which can tolerate up to 5% water by weight in the ethanol. Ethanol conversion is reduced when using an ethanol source with significant water content, but the reaction selectivity increases. The use of an ethanol feed comprising a small amount of water may be advantageous by allowing for the use a potentially less expensive ethanol source in the form of the ethanol/water azeotrope (about 4.4% water by weight). The effects of water are demonstrated in the Examples described herein.

Ethyl acetate can be produced from ethanol according to the following reactions:

(Eq. 1)

(Eq. 2)

In an embodiment, ethanol reacts in a single continuous reactive distillation column which provides sufficient residence time to achieve a relatively high conversion of ethanol. In an embodiment, the reactive distillation column may be configured to provide a conversion of ethanol of at least about 10% and a selectivity of at least about 60%, as described in more detail herein. Table 1 shows the effect of pressure on the boiling point of the pure components and azeotrope in the mixture. The azeotrope between ethanol and ethyl acetate is substantially avoided above a pressure of 13 atm.

Residue curve maps can be used to indicate feasible product compositions for distillation columns. In the presence of reaction along with separation, reactive residue curve maps can be used to determine feasible products from a reactive distillation column. Reactive residue curve maps at a pressure of 1 atm and 5 atm respectively are shown in FIG. 1. The stable nodes in the diagram are ethanol and ethyl acetate, and, therefore, it is possible to design a reactive distillation column where either ethanol or ethyl acetate can be obtained as the bottoms product. Hydrogen is an unstable node in the diagram and can be obtained as the distillate. Acetaldehyde and the ethanol/ethyl acetate azeotrope are saddle points in the diagram.

Figure 2:
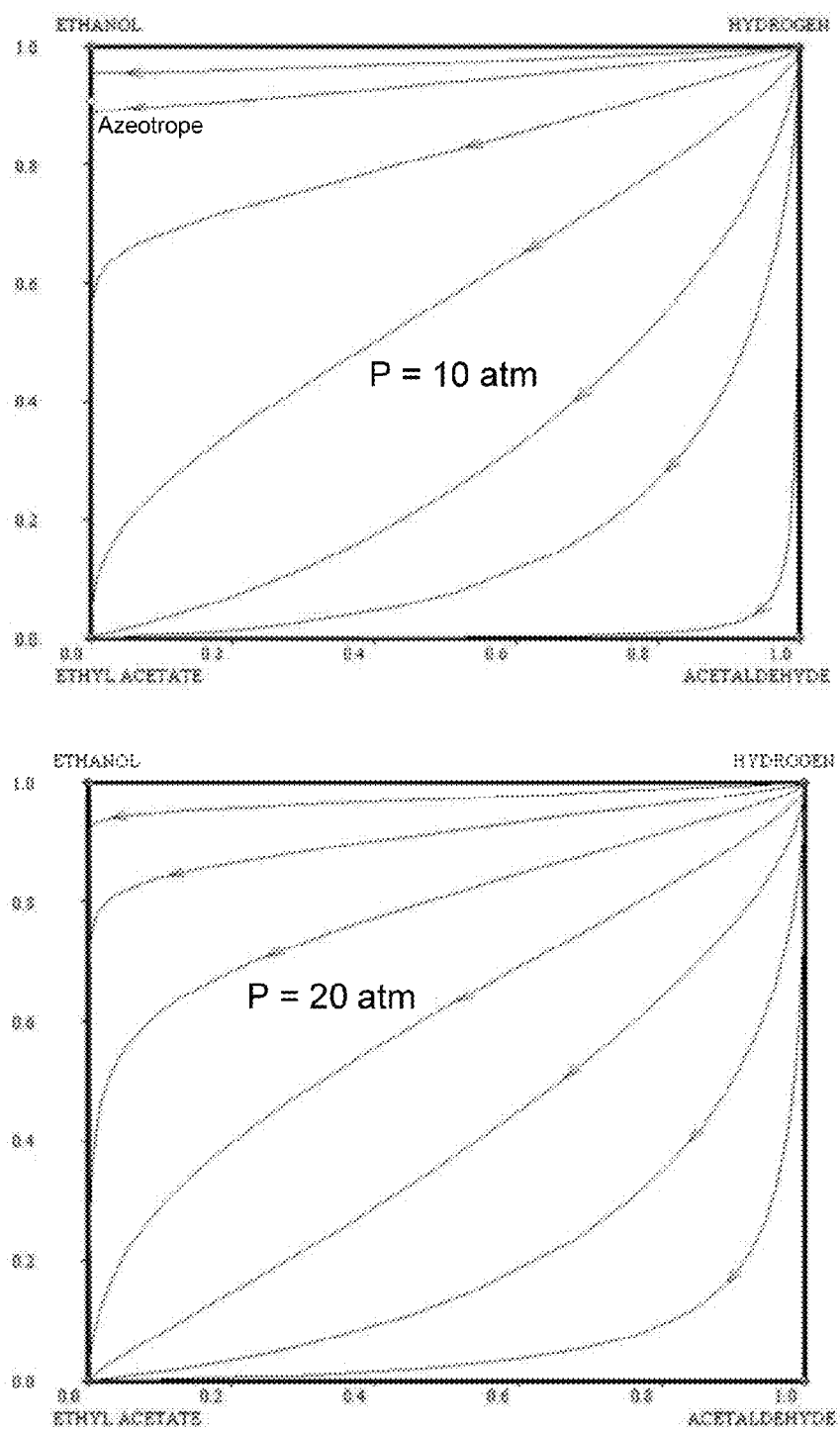
FIG. 2 shows reactive residue maps for conversion of ethanol to ethyl acetate at pressures of 10 and 20 atm for an embodiment.

Reactive residue curve maps at pressures of 10 atm and 20 atm respectively are shown in FIG. 2. The reactive residue curve maps for any pressure above 20 atm substantially similar to the reactive residue curve map at 20 atm.

In view of the reactive residue maps discussed above, a set of reactive distillation systems effective to produce high purity ethyl acetate from ethanol have been designed. The reactive distillation column can have single or multiple feed locations.

Reactive Distillation Column Configurations

The present systems and methods provide a reactive distillation system in which ethanol may be the sole or primary component of the feed. In some embodiments, the ethanol feed is used in conjunction with a separate, second feed of hydrogen. Reference to a "single feed" to a reactive distillation column means that the column has only one chemical feed stream supplying intended reactant(s) to the column. Nonetheless, such a single feed distillation column may have multiple entry points for the reactant, or recycling feed streams where a part of the reactant liquid or a partial distillate is drawn from the column and fed back into the column at a different point, e.g., to achieve improved separation and/or more complete reaction. A "single ethanol feed" thus refers to a single feed stream, in which ethanol is the sole or at least the primary constituent. In contrast, the term "dual feed" in the context of a distillation column refers to two separate chemical feed streams. For example, in some of the present embodiments, dual feeds are an ethanol feed and a separate hydrogen feed. The term "reactive distillation column" is used conventionally to refer to a distillation column in which both reaction and separation is performed. In this case, the primary and desired reaction is the conversion of two ethanol molecules to one ethyl acetate molecule with release of two hydrogen molecules. Thus, the present invention provides systems and methods for the production of ethyl acetate from ethanol which includes reacting ethanol over a suitable dehydrogenation and/or dimerization catalyst in a reactive distillation column, thereby producing ethyl acetate and hydrogen.

In an embodiment, a single reactive distillation column is used. Hydrogen gas is removed (e.g., continuously) from the top of the reactive distillation column as an overhead stream. Ethyl acetate is removed (e.g., continuously) from the bottom of the column as a bottoms stream. Optionally, contaminating byproducts present following reaction of the ethanol over the dehydrogenation catalyst can be reacted over a suitable hydrogenation catalyst in the lower part of the column or in a separate hydrogenation reactor. The hydrogenation can convert difficult to separate byproducts into species which are easier to separate from the ethyl acetate. Consequently, the process can also include purifying the ethyl acetate by distilling out resulting hydrogenated byproducts.

TABLE 1

Boiling point of reaction components.

| | Boiling Point, C. | | | | | |
|---|---|---|---|---|---|---|
| | P = 1 atm | P = 5 atm | P = 10 atm | P = 20 atm | P = 30 atm | P = 40 atm |
| Hydrogen | −161 | −137.6 | −123.7 | −106.5 | −94.3 | −84.5 |
| Acetaldehyde | 20.4 | 71.9 | 101.1 | 136.4 | 160.7 | 180 |
| Ethanol | 78.3 | 125.2 | 150.2 | 179 | 198 | 212.7 |
| Ethyl acetate | 77 | 136 | 169.6 | 210.3 | 238.4 | 260.7 |
| Ethanol/Ethyl acetate azeotrope | 71.7 | 123.5 | 150.1 | No Azeo | No Azeo | No Azeo |

In an embodiment, the reactive distillation column is configured for the dehydrogenation of ethanol with the formation of ethyl acetate. The reaction is accomplished by passing the ethanol feed stream over a dehydrogenation catalyst under conditions where ethyl acetate is formed and hydrogen and ethyl acetate are withdrawn as top and bottoms products respectively. Such product draws drive the thermodynamics of the process toward the desired products. In its simplest form, a reactive distillation system may comprise a reactor vessel operating with a liquid phase reaction in which hydrogen and/or other light gases are removed as the overhead product and a reaction product is removed as the bottoms product. Such a system may comprise a batch reactor in which hydrogen is removed during the reaction and the liquid product is removed after completion of the reaction to a desired degree of conversion.

Figure 3:
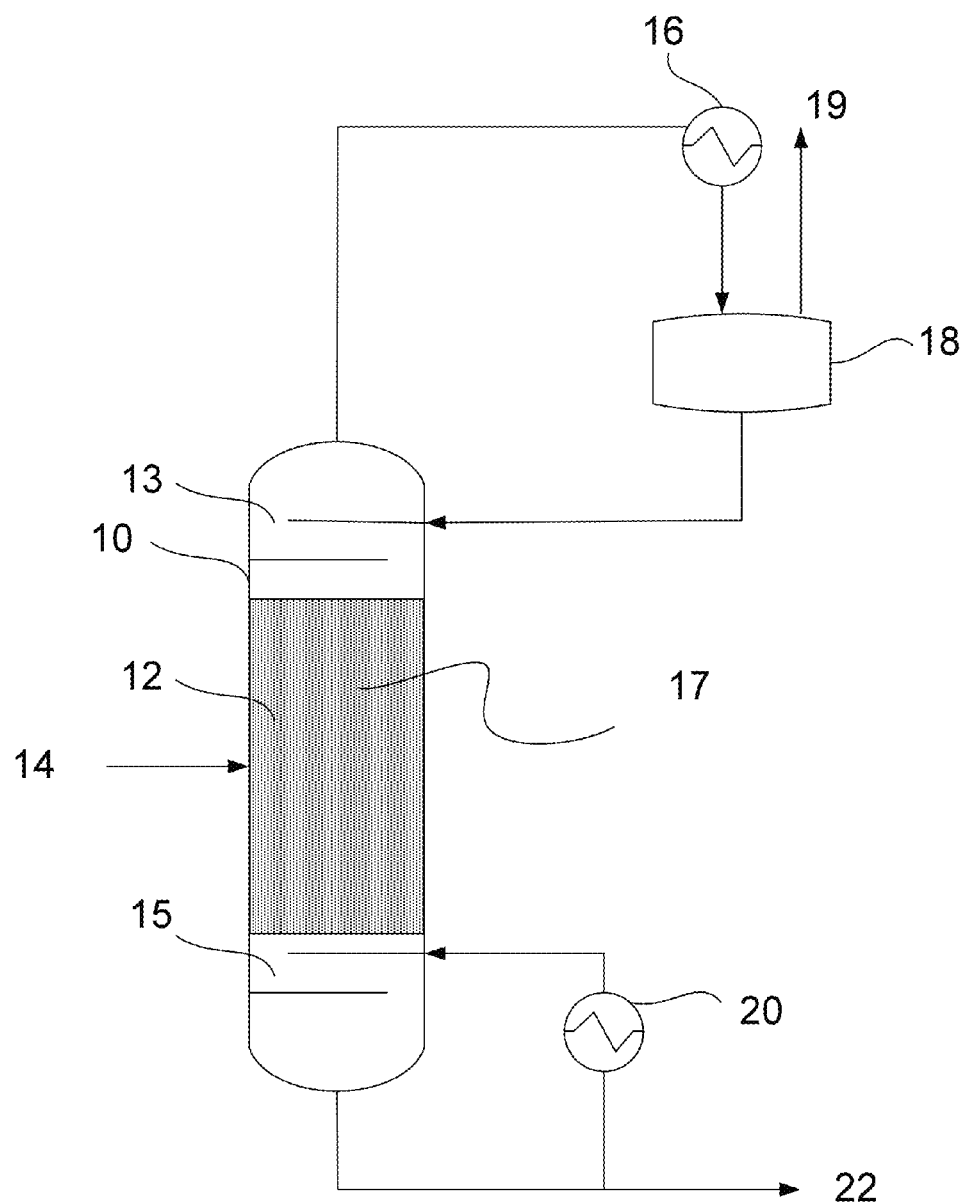
FIG. 3 shows a simplified schematic of a reactive distillation system according to an embodiment.

In an embodiment of a reactive distillation column, a reactive distillation column with a single feed of ethanol as shown schematically in FIG. 3 can produce hydrogen as a distillate and ethyl acetate as a bottoms product. Column 10 contains a generally central catalyst zone 12, and usually will include a top stage or non-reactive rectifying section 13 and a bottom state or non-reactive stripping section 15. Ethanol feed 14 is commonly fed to the middle part of the reactive distillation column. Distillate removed at the top of the column is passed through a partial condenser 16, and hydrogen is separated from lower boiling constituents in reflux tank 18. The hydrogen may leave the system as an overhead product stream 19, which in an embodiment may comprise trace amounts of additional components including ethanol, ethyl acetate, and/or one or more reaction byproducts. The condensed lower boiling constituents (i.e., reflux), or at least some portion thereof, can be cycled back to the column for further reaction and/or separation. The bottoms product can be passed through reboiler 20, where a portion of the bottoms product is evaporated and added back to the bottom of the column. The remaining bottoms product may pass out of the system as product stream 22. Alternatively, only a portion of the bottoms product may be passed through reboiler 20, with the vapor portion passing back to the bottom of the column and the remainder of the bottoms product being combined with any bottoms product bypassing the reboiler 20 and passing out of the system as product stream 22 for further processes and/or use as a final product. The product stream 22 may comprise the ethyl acetate produced in the column along with unreacted ethanol and potentially any side products produced by the reaction. The column reflux and reboil ratios are maintained such that essentially pure ethyl acetate is obtained as the bottoms product. In an embodiment, the bottoms product stream 22 may comprise greater than about 90%, greater than about 95%, greater than about 96%, greater than about 97%, greater than about 98%, greater than about 99%, or greater than about 99.5% ethyl acetate by weight.

During operation, the reactants and products flow through the reactor/column reacting and flashing along the length of the reactor/column. In an embodiment, the reaction of the reactants and/or products may occur in the catalyst zone 12, and the reactions may occur in the vapor and/or liquid phase. Specific catalysts useful in the reactive distillation systems and methods disclosed herein are discussed in more detail below. Ethyl acetate and hydrogen are produced due to the reaction over the dehydrogenation and dimerization catalyst. Acetaldehyde may also be produced during the reaction if the conversion of acetaldehyde to ethyl acetate is incomplete. The removal of the overhead stream 19 comprising hydrogen, which may occur by flashing, increases the extent of reaction. In general, the hydrogen concentration increases from the middle part of the column towards the top of the column. At pressures of about 13 bar or lower, as ethyl acetate is formed from the reactants, an azeotrope between ethyl acetate and ethanol occurs. This azeotrope may result in the overhead product 19 that leaves the top of the reactive distillation column 10 containing ethanol/ethyl acetate and/or acetaldehyde in addition to hydrogen. A partial condenser 16 allows hydrogen to be removed as a distillate, while acetaldehyde and ethanol are recycled back to the top of the reactive distillation column. At a pressure above about 13 atm, the ethyl acetate and ethanol azeotrope disappears, which improves the operation of the reactive distillation column.

The column 10 can be operated at any suitable pressure between about 1 atm and about 80 atm. In an embodiment, the column 10 may be operated at a pressure ranging from about 1 atm to about 5 atm, about 5 atm to about 10 atm, about 7 atm to about 12 atm, about 13 atm to about 15 atm, about 13 atm to about 20 atm, about 15 atm to about 20 atm, about 15 atm to about 30 atm, about 20 atm to about 30 atm, about 20 atm to about 50 atm, about 30 atm to about 40 atm, about 40 atm to about 50 atm, or about 50 atm to about 60 atm, about 60 atm to about 70 atm, about 60 atm to about 80 atm, or about 70 atm to about 80 atm. In an embodiment, the reactive distillation is performed at a pressure where ethanol-ethyl acetate azeotrope is not present. The temperature profile in the column is dictated by the mixture boiling point along the height of the column. In an embodiment the temperature within the column may range from about 100° C. to about 350° C., alternatively about 150° C. to about 250° C. The column 10 may comprise any number of stages equivalent to a number of theoretical stages sufficient to effect the reaction and separation of ethyl acetate to a desired purity. In an embodiment, the number of stages or the number of height equivalents of a theoretical plate (HETP) may range from about 1 to about 100, including for example from about 1 to about 10, about 10 to about 20, about 10 to about 50, about 20 to about 30, about 20 to about 70, about 30 to about 40, about 30 to about 50, about 30 to about 100, about 50 to about 70, about 50 to about 100, or about 70 to about 100. As described in more detail below, a relatively high conversion of ethanol to products can be achieved by the counter-current flow of reactants and products in addition to overcoming the reaction equilibrium by removal of products through the concurrent distillation within the column 10.

Figure 4:
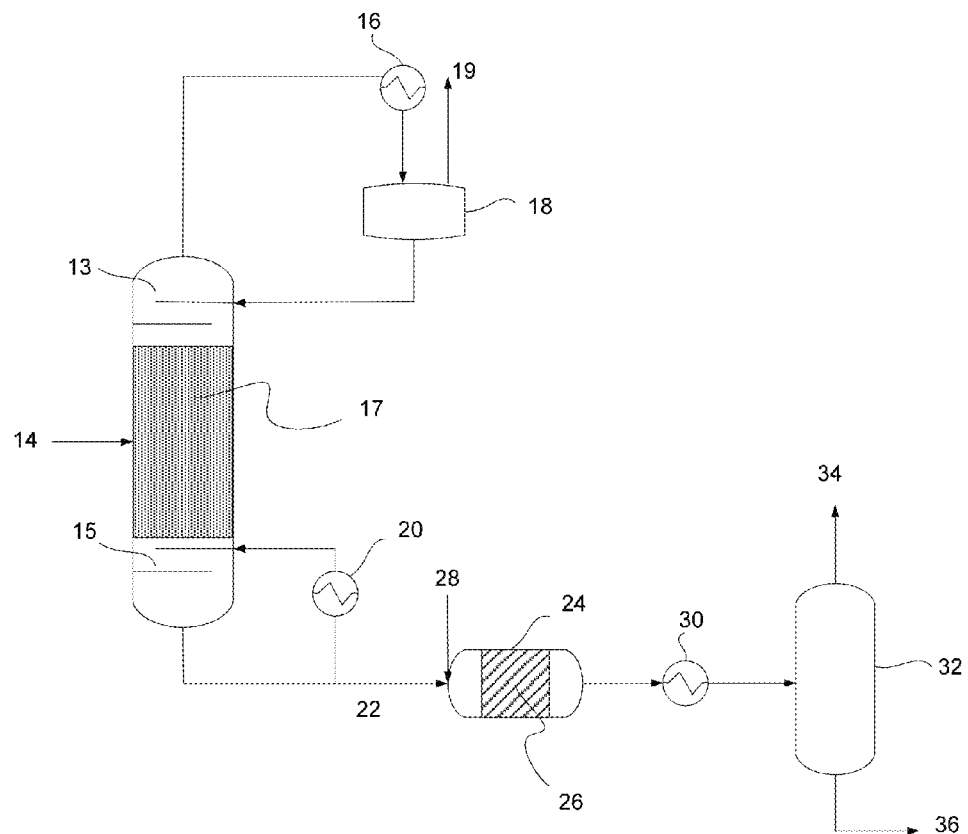
FIG. 4 shows a simplified schematic of a reactive distillation system according to another embodiment.

In an embodiment, the systems and methods may also include hydrogenating contaminants or reaction byproducts in the bottoms stream or in the reacted fluid after it has passed over the dehydrogenation catalyst and separating the hydrogenated contaminants or byproducts from the ethyl acetate. Aldehydes and/or ketones such as n-butyraldehyde and butan-2-one may be produced as byproducts in the reaction. These byproducts boil at temperatures close to the boiling point of ethyl acetate and may be difficult to separate from ethyl acetate. FIG. 4 shows a process schematic where the bottoms product 22 from the reactive distillation column 10 illustrated in FIG. 3 is sent to a hydrogenation reactor 24 comprising a hydrogenation catalyst 26 with a hydrogen co-feed 28. Suitable hydrogenation catalyst(s) may comprise various components and are described in more detail herein. At least a portion of the n-butyraldehyde and/or butan-2-one impurities can be hydrogenated and can then be separated using a separator 32. The separator 32 may comprise any of the types of separators described herein with respect to the reactive distillation system. Alternatively or in addition to the separators already described, the separator 32 may be a phase separator, which is a vessel that separates an inlet stream into a substantially vapor stream and a substantially liquid stream, such as a knock-out drum, flash drum, reboiler, condenser, or other heat exchanger. Such vessels also may have some internal baffles, temperature control elements, and/or pressure control elements, but generally lack any trays or other type of complex internal structure commonly found in columns. The separator also may be any other type of separator, such as a membrane separator. In a specific embodiment, the separator is a knockout drum. Finally, the separator may be any combination of the aforementioned separators arranged in series, in parallel, or combinations thereof. In an embodiment, separator 32 comprises a distillation column. The outlet of the hydrogenation reactor 24 may be passed through a heat exchanger 30 (e.g., a condenser) and cooled before entering the separator 32. The heat exchanger 30 may be any equipment suitable for heating or cooling one stream using another stream. Generally, the heat exchanger 30 is a relatively simple device that allows heat to be exchanged between two fluids without the fluids directly contacting each other. Examples of suitable heat exchangers 30 include, but are not limited to, shell and tube heat exchangers, double pipe heat exchangers, plate fin heat exchangers, bayonet heat exchangers, reboilers, condensers, evaporators, and air coolers. In the case of air coolers, one of the fluids comprises atmospheric air, which may be forced over tubes or coils using one or more fans.

The bottoms product stream 36 from the separator 32 may comprise ethyl acetate and may have a purity of greater than about 90%, greater than about 95%, greater than about 96%, greater than about 97%, greater than about 98%, greater than about 99%, or greater than about 99.5% ethyl acetate by weight. Unconverted hydrogen and the hydrogenated byproducts may be removed as an overhead product 34, and may be used, for example, as fuel or a feed to one or more processes. In an embodiment, the separator 32 may be operated between a pressure of 1 atm and 80 atm.

In an embodiment, the bottoms product stream 36 may pass to another separator. The separator may then separate the bottoms product stream into an ethyl acetate stream and a byproduct stream comprising one or more heavier hydrogenation products produced in the hydrogenation reactor 26. This separation scheme may allow the resulting ethyl acetate stream to have a purity of greater than about 90%, greater than about 95%, greater than about 96%, greater than about 97%, greater than about 98%, greater than about 99%, or greater than about 99.5% ethyl acetate by weight.

Figure 5:
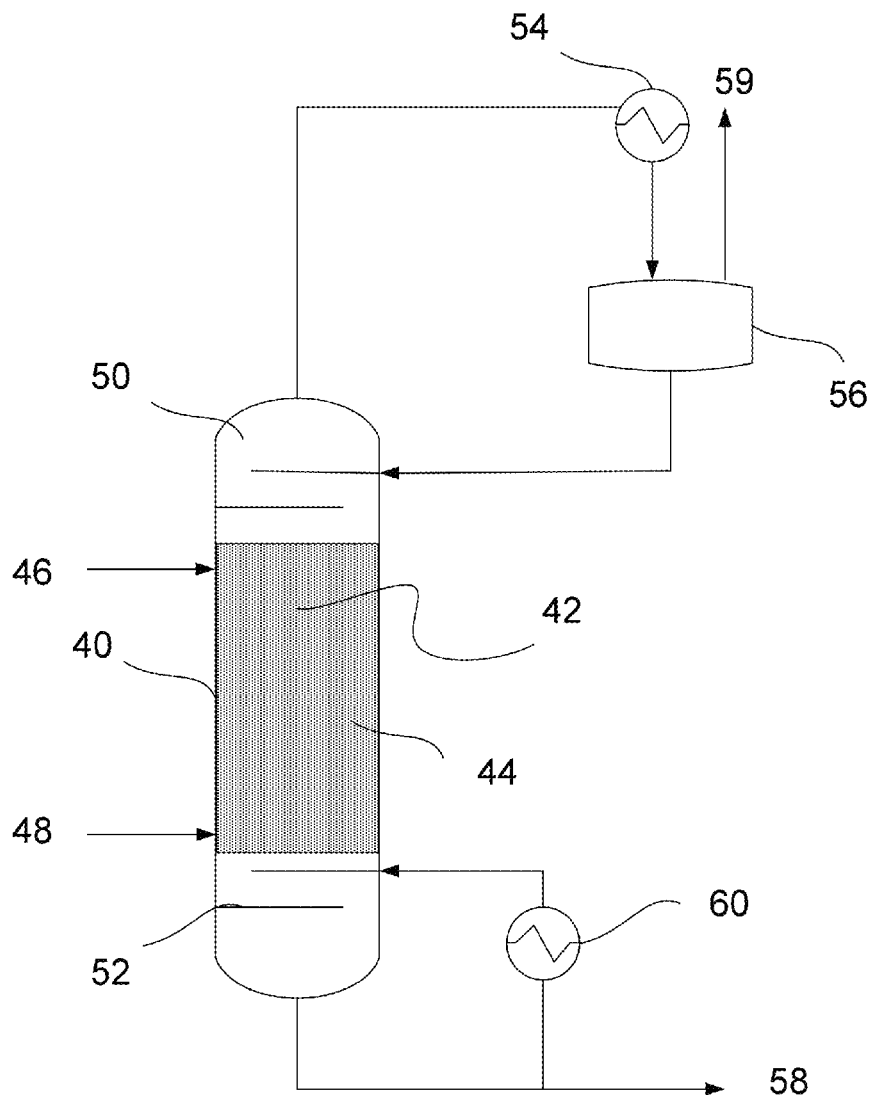
FIG. 5 shows a simplified schematic of a reactive distillation system according to still another embodiment.

In another embodiment of the invention, the reactive distillation column has two feeds. Ethanol may be fed to the upper part of the column (upper feed), and hydrogen may be fed to the lower part of the column (lower feed). A schematic for the double feed reactive distillation column is schematically illustrated in FIG. 5. This system includes column 40 containing catalyst 42 in catalyst zone 44, and commonly may include a top stage or non-reactive rectifying section 50 and a bottom stage or non-reactive stripping section 52. In the illustrated system, ethanol feed 46 is delivered at or near the top of the catalyst zone 44, and the hydrogen feed 48 is delivered at or near the bottom of catalyst zone 44. It should be recognized columns can be designed with the ethanol feed 46 location in other locations, e.g., within the catalyst zone 44 but above the hydrogen feed 48, such as from the approximate middle of the catalyst zone 44 to the top of the column 40. Similarly, columns with the hydrogen feed 48 in other locations can also be designed, e.g., with the hydrogen feed 48 from the approximate middle of the catalyst zone 44 to the bottom of the column 40 or even higher within the catalyst zone 44 but below the ethanol feed 46. In an embodiment, the ethanol feed 46 and the hydrogen feed 48 are separated sufficiently to allow byproduct hydrogenation to be substantially completed before hydrogen from the feed reaches substantial concentrations of ethanol being dehydrogenated. Ethanol reacts over the catalyst producing ethyl acetate and hydrogen. Examples of suitable dehydrogenation and dimerization catalysts are described in more detail herein.

Due to boiling point differences, hydrogen moves towards the top of the column 40 and ethyl acetate moves towards the bottom of the column 40. Acetaldehyde may be produced during the reaction and may move up in the column 40. At least a portion of the acetaldehyde, if present, can be condensed in condenser 54 (e.g., a partial condenser, or a total condenser), passed through reflux tank 56, and recycled back to column 40 as reflux. A product stream 59 comprising hydrogen is taken out as distillate from the reflux tank 56. A part of the bottom draw is taken out as the ethyl acetate product stream 58, while the remaining part is passed through reboiler 60 to be recycled to the column 40. In an embodiment, the bottom draw may be passed through a reboiler (e.g., similar to reboiler 60) and optionally passed to a separator where the vapor portion may pass to the column 40 while at least a portion of the remainder is taken out as the ethyl acetate product stream 58. The stream passing through the reboiler 60 provides the evaporation effect and vapor flow for operating the column 40. The product stream 58 may comprise the ethyl acetate produced in the column along with unreacted ethanol and potentially any side products produced by the reaction.

Byproducts such as n-butyraldehyde and butan-2-one produced in the reaction may have boiling points close to the boiling point of ethyl acetate. The lower hydrogen feed 48 is useful in hydrogenating the by-products to produce components that can be separated easily from ethyl acetate. The ratio of the hydrogen feed to the ethanol feed can beneficially be adjusted to minimize the amount of close boiling byproducts, while not excessively reducing ethyl acetate to ethanol. In an embodiment, the molar ratio of ethanol to hydrogen ranges from about 1:10 to about 1000:1, e.g., from about 1:10 to about 1:1, from about 1:1 to about 5:1, from about 1:1 to about 10:1, from about 5:1 to about 25:1, from about 5:1 to about 50:1, from about 10:1 to about 50:1, from about 10:1 to about 100:1, from about 50:1 to about 200:1, from about 50:1 to about 400:1, from about 100:1 to about 500:1, from about 100:1 to about 1000:1, from about 200:1 to about 1000:1, or from about 500:1 to about 1000:1. Hydrogen product from the reaction leaves at the top of the column. In an embodiment, the column 40 may operate at any of the conditions (e.g., operating pressure, operating temperature, etc.) discussed herein with respect to column 10 in FIG. 3. In addition, the column 40 may have any number of stages, and in an embodiment have any number of stages as described with respect to column 10 in FIG. 3.

Figure 6:
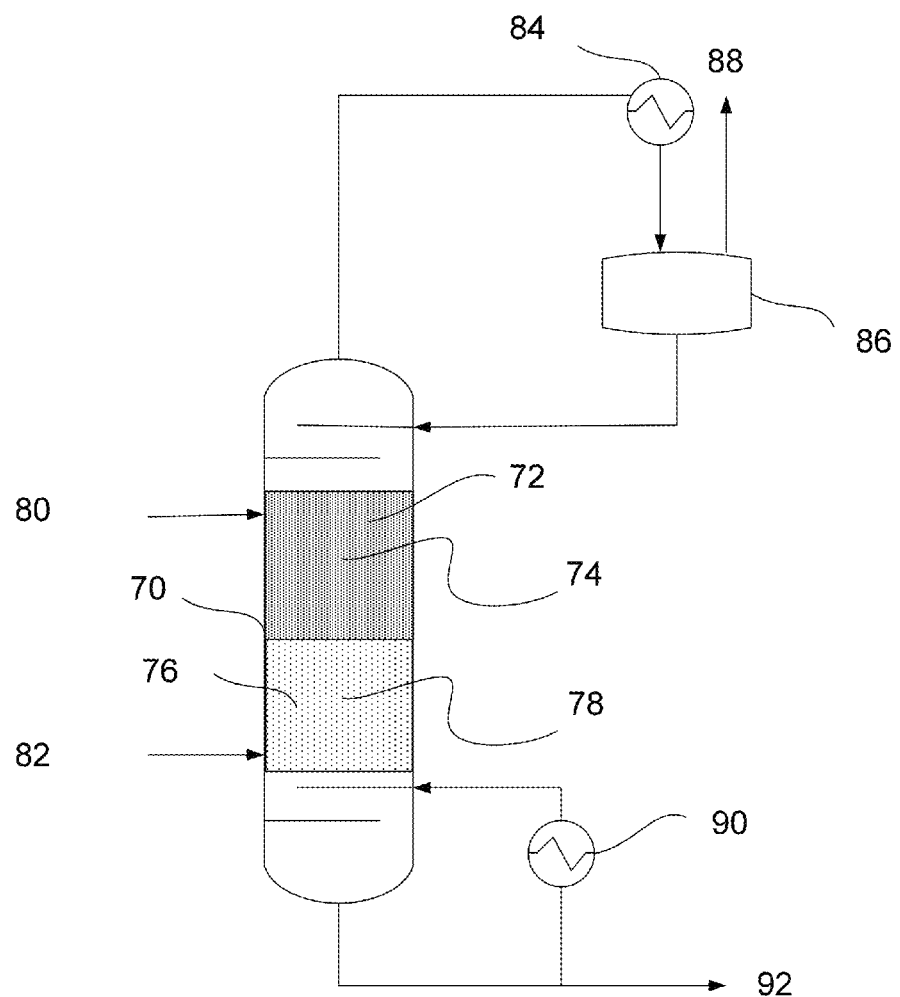
FIG. 6 shows a simplified schematic of a reactive distillation system according to yet another embodiment.

As schematically illustrated in FIG. 6, the reactive distillation column 70 has two feeds 80, 82 and uses two catalyst zones, identified as an upper zone 72 containing Catalyst A 74 and a lower catalyst zone 76 containing Catalyst B 78. Ethanol feed 80 is fed to the upper part of the column 70 (upper feed). Hydrogen feed 82 is fed to the lower part of the column 70 (lower feed). The molar ratio of ethanol to hydrogen may fall within any of the ranges described above with respect to FIG. 5 (e.g., from about 1:10 to about 1000:1, and all sub-ranges). Ethanol may react over the upper catalyst (Catalyst A 74) producing ethyl acetate and hydrogen. Examples of suitable upper catalysts are described in more detail herein with respect to the dehydrogenation and dimerization catalysts. As with previous schematic designs shown, the column 70 will usually include a top stage or non-reactive rectifying section 71 and a bottom state or non-reactive stripping section 79.

Due to boiling point differences, hydrogen moves towards the top of the column 70 and ethyl acetate moves towards the bottom of the column 70. Acetaldehyde may be produced during the reaction and may move up in the column 70. At least a portion of the acetaldehyde, if present, can be condensed in condenser 84 and recycled back to the reaction zone through reflux tank 86. Byproducts such as n-butyraldehyde and butan-2-one produced in the reaction can have boiling points close to the boiling point of ethyl acetate. The lower hydrogen feed is useful in hydrogenating the by-products over the lower catalyst (Catalyst B) to produce components that can be separated easily from ethyl acetate. Examples of hydrogenation catalysts (Catalyst B) are described in more detail herein. A product stream 88 comprising hydrogen from the reaction leaves at the top of the column 70. A portion of the bottom draw is taken out as the ethyl acetate product stream 92, while the remaining portion is passed through reboiler 90 to be recycled to the column 70. In an embodiment, the bottom draw may be passed through a reboiler (e.g., similar to reboiler 90) and optionally passed to a separator where the vapor portion may pass to the column 70 while at least a portion of the remainder is taken out as the ethyl acetate product stream 92. The stream passing through the reboiler 90 provides the evaporation effect and vapor flow for operating the column 70. The product stream 92 may comprise the ethyl acetate produced in the column along with unreacted ethanol and potentially any side products produced by the reaction. Subsequent purification of product stream 92 comprising ethyl acetate may be needed to remove the hydrogenated byproducts from the ethyl acetate, e.g., using a separator such as that as shown in FIG. 4 as separator 32, which in an embodiment may comprise a distillation column.

In an embodiment, the column 70 may operate at any of the conditions (e.g., operating pressure, operating temperature, etc.) discussed herein with respect to column 10 in FIG. 3. In addition, the column 70 may have any number of stages, and in an embodiment have any number of stages as described with respect to column 10 in FIG. 3.

In the dual feed systems described above with respect to FIGS. 5 and 6, the hydrogen feed should be at a sufficiently low level that it does not significantly adversely affect the dehydrogenation of ethanol in the zone above, while being effective to hydrogenate the undesirable close boiling point byproducts. Feed rates of hydrogen can be adjusted empirically to optimize this balance. Commonly, the ratio of ethanol:hydrogen will be in a range of about 500:1 to 1:1 molar ratio, more commonly about 500:1 to 10:1 or 500:1 to 100:1.

In an embodiment, side reactors can be connected to a reactive distillation column to increase the catalyst holdup for improved reactant conversion. In the side reactor embodiment, the side reactor feed is withdrawn from the distillation column and the reactor effluent is returned back to the same column. An adequate amount of catalyst may be arranged in a side reactor system where traditional reactor types and catalyst structures can be used. Also, the reaction conditions within the side reactor such as temperature can be adjusted independently of those prevailing in the distillation column by appropriate heat exchange.

Figure 7:
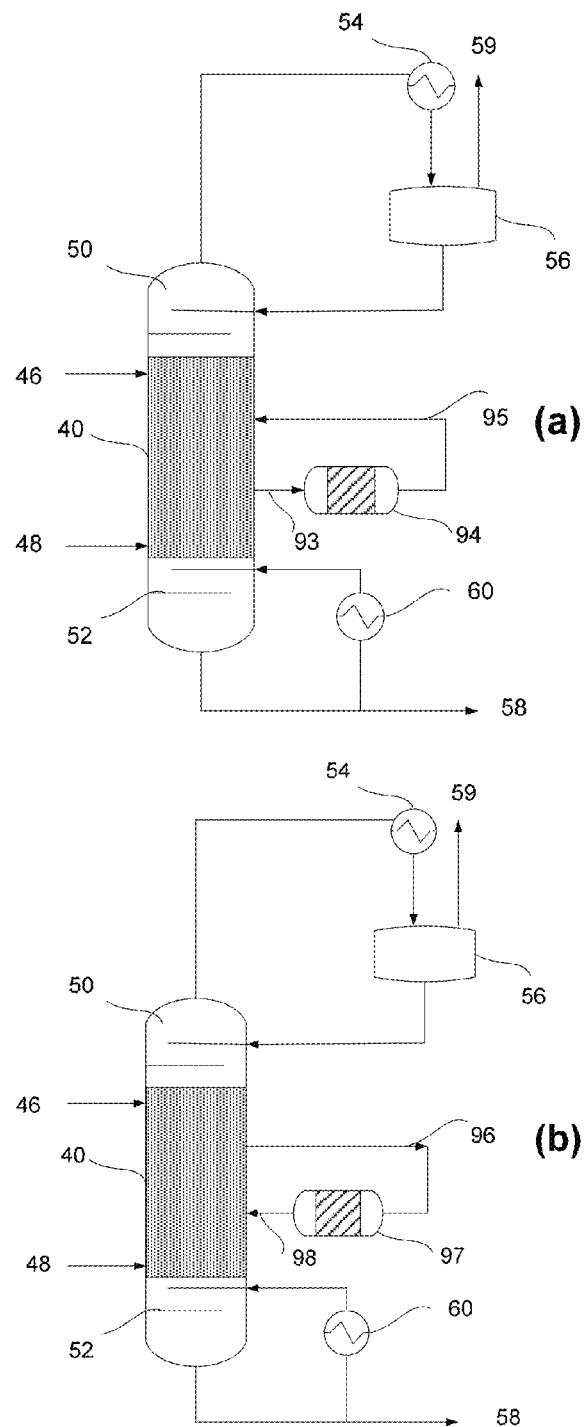
FIGS. 7(a) and 7(b) shows a simplified schematic of a reactive distillation system according to an embodiment.

Schematics for a side reactor reactive distillation column with a single catalyst are shown in FIG. 7. A single side reactor is shown, however, multiple side reactors along the length of the reactive distillation column can be used. FIG. 7(*a*) shows a configuration where the feed 93 to the side reactor 94 is bottom up and vapor phase. The outlet from side reactor 94 is stream 95 which is sent back to the distillation column 40 at any location in the column 40 above the location of feed 93. FIG. 7(*b*) shows a configuration where the feed 96 to the side reactor 97 is top down and liquid phase. The outlet from side reactor 97 is stream 98 which is sent back to the distillation column 40 at any location in the column 40 below the location of feed 96. The side reactors 94 and 97 each contain catalyst for converting ethanol into ethyl acetate. Examples of suitable catalysts are described in more detail herein.

The use of a side reactor using a liquid feed may allow for the reaction to occur in the liquid phase. While not intending to be limited by theory, it is believed that the dehydrogenative dimerization of ethanol to ethyl acetate may occur over the dehydrogenation and dimerization catalysts described herein in the liquid phase. It has not been previously recognized that the dehydrogenation and dimerization conversion of ethanol to ethyl acetate would occur in the liquid phase. The use of a liquid phase reaction may allow for reactive distillation to be effectively used for converting ethanol into ethyl acetate and hydrogen.

While illustrated as a bottom up vapor phase design and a top down liquid phase design in FIGS. 7(*a*) and 7(*b*), the side reactors 94, 97 may also operate bottom up using a liquid phase draw from the column 40 and top down using a vapor phase draw from the column with the appropriate equipment such as pumps, compressors, valves, piping, etc. In an embodiment, the side reactors 94, 97 may be implemented as a single reactor vessel, or as a plurality of reactor vessels arranged in series and/or parallel. In an embodiment, a plurality of side reactors may be implemented as shown in FIGS. 7(*a*) and 7(*b*) along the length of the column as needed. In addition, the catalyst in both the column 40 and the side reactor 94 may convert ethanol into ethyl acetate, though the specific catalysts (e.g., catalyst compositions, catalyst forms, and/or catalyst component loadings) in each of the column 40 and the side reactor 94, 97 may be the same or different. Suitable catalysts for converting ethanol into ethyl acetate may be selected based on the expected operating conditions, which may vary between the column 40 and the side reactor 94, 97.

Figure 8:
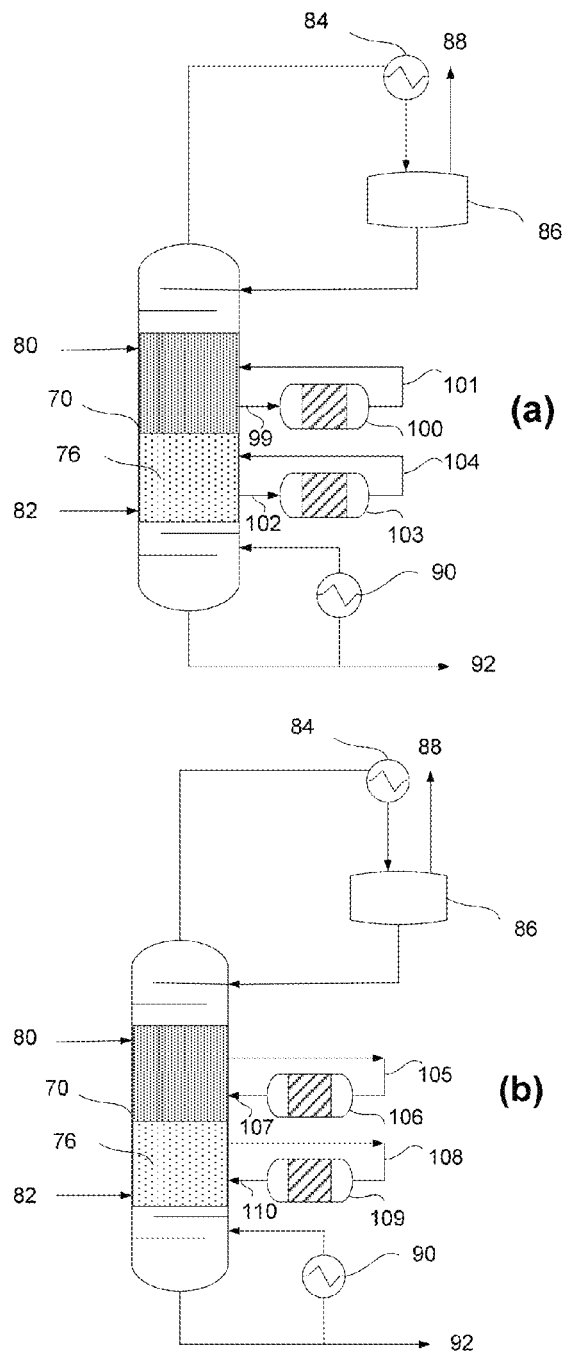
FIGS. 8(a) and 8(b) shows a simplified schematic of a reactive distillation system according to another embodiment.

Schematics for a side reactor reactive distillation with two feeds and using two distinct catalyst zones are shown in FIG. 8. A single side reactor is shown for each catalyst zone in the reactive distillation column 70, however, multiple side reactors along the length of the reactive distillation column 70 can be used for each catalyst zone. FIG. 8 (*a*) shows a configuration where the top zone feed 99 to the side reactor 100 is bottom up and vapor phase. The bottom zone feed 102 to another side reactor 103 is also bottom up and vapor phase. The outlet from side reactor 100 is stream 101 which is sent back to the distillation column at any location in the column above the location of feed 99. The outlet from side reactor 103 is stream 104 which is sent back to the distillation column at any location in the column above the location of feed 102. FIG. 8 (*b*) shows a configuration where the top zone feed 105 to the side reactor 106 is top down and liquid phase. The bottom zone feed 108 to another side reactor 109 is also top down and liquid phase. The outlet from side reactor 106 is stream 107 which is sent back to the distillation column at any location in the column below the location of feed 105. The outlet from side reactor 109 is stream 110 which is sent back to the distillation column at any location in the column below the location of feed 108. Examples of suitable catalysts for side reactors 100 and 106 may include may include any of the dehydrogenation and dimerization catalysts described in more detail herein. Examples of hydrogenation catalysts for side reactors 103 and 109 include any of the hydrogenation catalysts described in more detail herein.

While illustrated as a bottom up vapor phase design and a top down liquid phase design in FIGS. 8(a) and 8(b), the side reactors 100, 103, 106, 109 may also operate bottom up using a liquid phase draw from the column 70 and top down using a vapor phase draw from the column 70 with the appropriate equipment such as pumps, compressors, valves, piping, etc. In an embodiment, the side reactors 100, 103, 106, 109 may be implemented as a single reactor vessel, or as a plurality of reactor vessels arranged in series and/or parallel. In an embodiment, a plurality of side reactors may be implemented as shown in FIGS. 8(a) and 8(b) along the length of the column as needed. In addition, the respective catalysts in both the column 70 and the side reactors 100, 106 may convert ethanol into ethyl acetate, though the specific catalysts (e.g., catalyst compositions, catalyst forms, and/or catalyst component loadings) in each of the column 40 and the side reactors 100, 106 may be the same or different. Suitable catalysts for converting ethanol into ethyl acetate may be selected based on the expected operating conditions, which may vary between the column 40 and the side reactors 100, 106. Similarly, the respective catalysts in both the column 70 and the side reactors 103, 109 may comprise hydrogenation catalysts, though the specific catalysts (e.g., catalyst compositions, catalyst forms, and/or catalyst component loadings) in each of the column 70 and the side reactors 103, 109 may be the same or different. Suitable hydrogenation catalysts may be selected based on the expected operating conditions, which may vary between the column 70 and the side reactors 100, 106.

Figure 9:
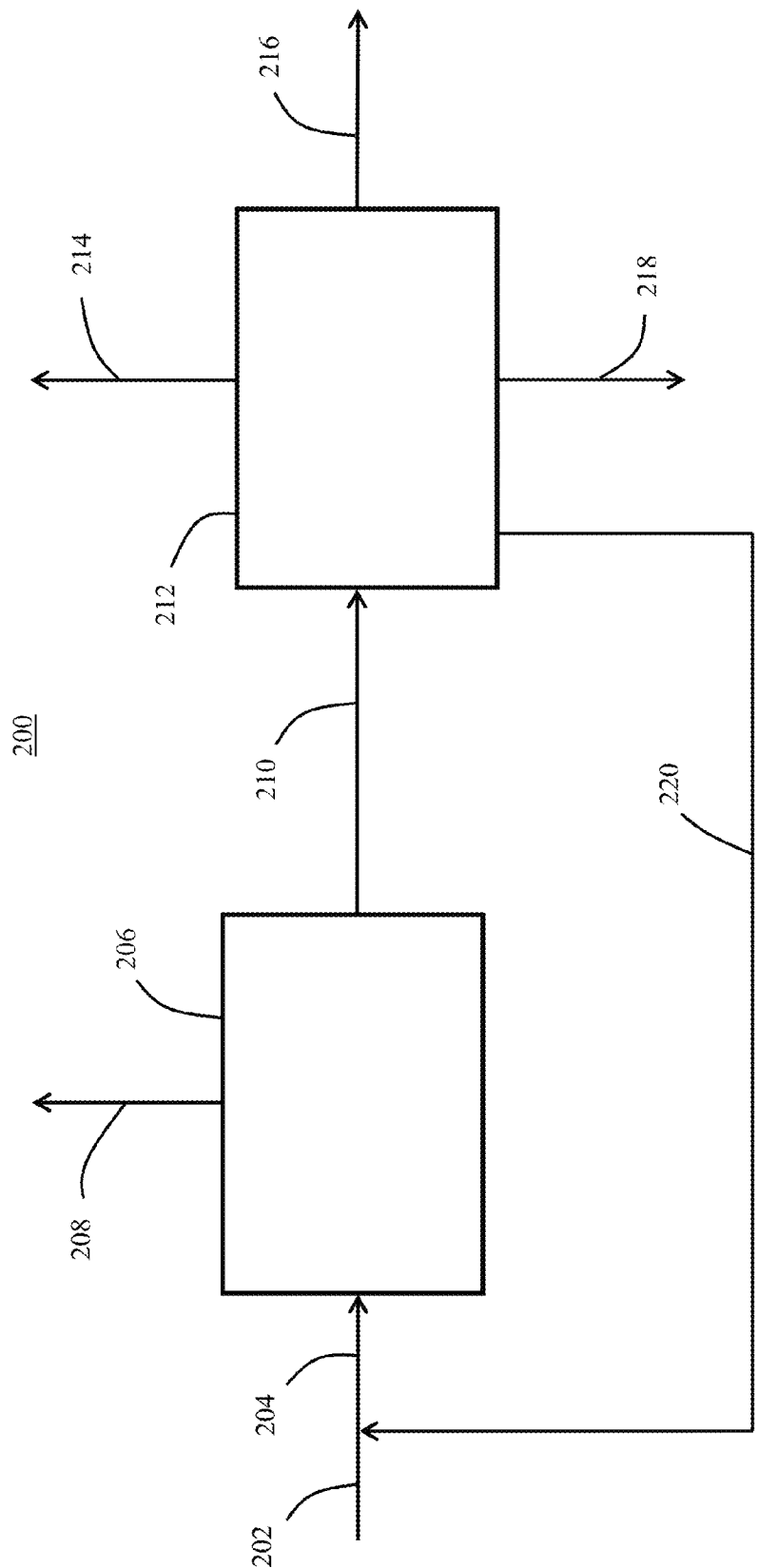
FIG. 9 illustrates a schematic flow diagram of a reactive distillation system with a recycle according to an embodiment.

As schematically illustrated in FIG. 9, an ethyl acetate production process may comprise a products separation section for use in separating the product stream and allowing at a least a portion of any unreacted ethanol to be recycled to the inlet of the process. The products separation section may be configured to provide at least one product stream comprising ethyl acetate having a purity of greater than about 90%, greater than about 95%, greater than about 96%, greater than about 97%, greater than about 98%, greater than about 99%, or greater than about 99.5% ethyl acetate by weight. At least one additional stream may be produced comprising the remaining components of the product stream from the reactive distillation column. In an embodiment, a plurality of streams are produced in the separation section comprising a stream predominantly comprising ethyl acetate, a stream comprising hydrogen, a stream comprising ethanol, and/or a heavies stream comprising one or more reaction products with boiling points above the boiling point of ethyl acetate. In an embodiment, the stream comprising ethanol may be recycled to the reactive distillation column. In an embodiment, at least a portion of the stream comprising hydrogen may be recycled to the reactive distillation column to provide at least a portion of the hydrogen feed.

As schematically illustrated in FIG. 9, a system 200 for producing ethyl acetate may comprise a feed stream 202 comprising ethanol that may be combined with a recycle stream 220 comprising ethanol to form the inlet stream 204 to the reactive distillation system 206. The system 200 may be useful for embodiments in which there is an incomplete conversion of ethanol in the reactive distillation system 208. While illustrated as being combined prior to introduction to the reactive distillation system 206, the feed stream 202 and the recycle stream 220 may be fed individually to the reactive distillation system 206. In an embodiment, the reactive distillation system 206 may comprise any of the reactive distillation systems described with respect to FIG. 3-8 herein. The reactive distillation system may produce an overhead product stream 208 and a bottoms product stream 210. The overhead product stream 208 may comprise hydrogen and may generally correspond to any of the streams 19, 59, and/or 88 as illustrated in FIGS. 3-8. Similarly, the bottoms product stream 210 may comprise ethyl acetate and at least a portion of any unreacted ethanol and/or additional reaction products, and the bottoms product stream 210 may generally correspond to any of the streams 22, 36, 58, and/or 92 as illustrated in FIGS. 3-8.

A products separation section 212 may receive the bottoms product stream 210 from the reactive distillation system 206, and, in some embodiments, the overhead product stream 208. The products separation section 212 may comprise any number or type of separation units, which may employ pressure- or temperature-swing distillation, pressure- or temperature-swing adsorption, membrane-based separation, cryogenic distillation, and/or any other suitable separation technology, all of which may be used to generate a desired product distribution. The products separation section 212 may generally produce an ethyl acetate product stream 216. The ethyl acetate product stream 216 may comprise ethyl acetate having a purity of greater than about 90%, greater than about 95%, greater than about 96%, greater than about 97%, greater than about 98%, greater than about 99%, or greater than about 99.5% ethyl acetate by weight. In addition to the ethyl acetate product stream 216, one or more additional streams may be produced by the products separation section 212. In an embodiment, a lights product stream 214 may be produced. The lights product stream 214 may comprise hydrogen and minor amounts of ethanol and/or other light components. In an embodiment, a heavies product stream 218 may comprise one or more reaction products (e.g., butanol, one or more aldehydes and/or ketones, etc.). In an embodiment, a recycle stream 220 may be produced. The recycle stream may comprise ethanol for use as a feed for the reactive distillation system 206. In some embodiments, the ethanol stream may not be recycled to the reactive distillation system, but rather may exit the system 200 as a separate product stream. Each of the potential product streams 214, 216, 218, and/or 220 may exit the system as separate product stream and/or exit the system 200 for use as fuel and/or as a feed to additional downstream processes. While illustrated as separate streams 214, 216, 218, and/or 220, one or more of these streams may exit the system 220 as a combined product stream.

In an embodiment illustrated in FIG. 10, a product separation system may comprise a plurality of separation units coupled to the reactive distillation system 113. In this embodiment, the reactive distillation system 113 may be the same or similar to the reactive distillation system 206 described above with respect to FIG. 9. A feed stream 111 comprising ethanol enters the reaction distillation system 113 along with a recycle stream 127. A product stream may be produced from the reactive distillation system 113 and cooled in heat exchanger 114. Stream 112 contains light boiling components such as $H_2$ and may pass out of the reactive distillation system 113. Heat exchanger 114 may comprise any of the heat exchanger types described herein. The product stream passing out of the heat exchanger 114 may pass to separator 117. The separator 117 may comprise any of the types of separators described herein, and in an embodiment, may comprise a phase separator of any of the types described herein. The separator 117 may produce a vapor stream 115 and a liquid stream 116. Vapor stream 115 predominantly comprises hydrogen, and the liquid stream 116 comprises higher boiling components. The separator 117 may operate at a pressure ranging from about 1 atm to about 80 atm.

The liquid stream 116 passes to separator 120. Separator 120 may comprise any of the types of separators described herein, and, in an embodiment, comprises a distillation column. The separator 120 may generally operate at a pressure of between about 1 atm to about 30 atm, and in an embodiment, may operate at a pressure of less or equal to about 5 atm. In an embodiment, separator 120 operates at a pressure below the pressure of separator 122 as described below. The temperature profile in the column may be dictated by the mixture boiling point along the height of the column. The separator 120 may separate the liquid stream 116 into an overhead stream and a bottoms stream 119. The overhead stream may pass through a heat exchanger and separator to produce a vapor overhead stream 121 and a liquid overhead stream 118. The vapor overhead stream 121 may comprise hydrogen and ethanol. The vapor overhead stream 121 can be used as fuel within the system, and/or the overhead stream 121 can be recycled within the system for use as a feed to the reactive distillation system 113. The liquid overhead stream 118 may predominantly comprise ethanol and ethyl acetate. The bottoms stream 119 may predominantly comprise ethanol in addition to minor amounts of ethyl acetate, butanol, and/or additional reaction products.

Bottoms stream 119 may pass to a separator 125. Separator 125 may comprise any of the separators described herein, and, in an embodiment, separator 125 comprises a distillation column. Separator 125 may separate the bottoms stream 119 into an overhead stream 127 comprising ethanol and a bottoms stream 126 comprising the higher boiling components including butanol. Overhead stream 127 may be recycled to the reactive distillation system 113 for use a feed to the ethyl acetate production system. The bottoms stream 126 may exit the system for use as fuel, as a final product, and/or as a feed to one or more suitable downstream processes.

The liquid overhead stream 118 from separator 120 may pass to separator 122. Separator 122 may comprise any of the separators described herein, and, in an embodiment, comprises a distillation column. Separator 122 may operate at a higher pressure than separator 120. In an embodiment, separator 122 may operate a pressure of greater than about 160%, greater than about 200%, greater than about 250%, greater than about 300%, greater than about 400%, greater than about 500%, greater than about 600%, or greater than about 700% of the pressure of separator 120. In an embodiment, separator 122 may operate between about 8 atm and 80 atm, including between about 8 atm and about 20 atm, between about 15 atm and about 40 atm, between about 35 atm and about 60 atm, or between about 50 atm and about 80 atm. The increased operating pressure of separator 122 relative to separator 120 may provide for an improved separation of the components in the liquid overhead stream 118. Separator 122 may separate the liquid overhead stream 118 into an overhead stream 123 and a bottoms stream 124. Overhead stream 123 may comprise ethanol, ethyl acetate, and/or acetaldehyde in addition to other reaction products. Overhead stream 123 may pass back to separator 120 for further separation of the components. The bottoms stream 124 may comprise ethyl acetate as a product stream. In an embodiment, the bottoms stream 124 may comprise greater than about 90%, greater than about 95%, greater than about 96%, greater than about 97%, greater than about 98%, greater than about 99%, or greater than about 99.5% ethyl acetate by weight.

The product separation system illustrated in FIG. 10 produces an ethyl acetate product stream 124, a first lights product stream 112, a second lights product stream 115, a third lights product stream 121, a heavies product stream 126, and a recycle stream 127 comprising ethanol. Some portion of the lights streams 112, 115, 121 may be recycled back to the reactive distillation system 113 for use as a hydrogen and/or ethanol feed. While illustrated as a separate feed to the reactive distillation system, the recycle stream 127 may be combined with the feed stream 111 comprising ethanol prior to the combined stream entering the reactive distillation system 113.

In an embodiment illustrated in FIG. 11, another product separation system may comprise a plurality of separation units coupled to a reactive distillation system 129. In this embodiment, the reactive distillation system 129 may be the same or similar to the reactive distillation system 206 described above with respect to FIG. 9. A feed stream 128 comprising ethanol enters the reaction distillation system 129 along with a recycle stream 141. Stream 140 contains light boiling components such as $H_2$ and may pass out of the reactive distillation system 129. A product stream may be separated from the reactive distillation system 129 and cooled in heat exchanger 130. Heat exchanger 114 may comprise any of the heat exchanger types described herein. The product stream passing out of the heat exchanger 130 may pass to separator 133. The separator 133 may comprise any of the types of separators described herein, and in an embodiment, may comprise a phase separator of any of the types described herein. The separator 133 may separate the product stream into a vapor stream 131 and a liquid stream 132. Vapor stream 131 may predominantly comprise hydrogen, and the liquid stream 132 may comprise higher boiling components. The separator 133 may operate at a pressure ranging from about 1 atm to about 80 atm.

The liquid stream 132 passes to separator 134. Separator 134 may comprise any of the types of separators described herein, and, in an embodiment, comprises a distillation column. The separator 134 may generally operate at a pressure of between about 1 atm to about 80 atm, and the temperature profile in the column may be dictated by the mixture boiling point along the height of the column. The separator 134 may separate the liquid stream 132 into an overhead stream and a bottoms stream 119. The overhead stream may pass through a heat exchanger and separator to produce a vapor overhead stream 135 and a liquid overhead stream 141. The vapor overhead stream 135 may comprise hydrogen and ethanol. The vapor overhead stream 135 can be used as fuel within the system, and/or the overhead stream 135 can be recycled within the system for use as a feed to the reactive distillation system 129. The liquid overhead stream 141 may predominantly comprise ethanol, and may be recycled to the reactive distillation system 129 for use a feed to the ethyl acetate production system. The bottoms stream 136 may comprises ethyl acetate, butanol, and/or additional reaction products.

The bottoms stream 136 from separator 134 may pass to separator 137. Separator 137 may comprise any of the separators described herein, and, in an embodiment, comprises a distillation column. In an embodiment, separator 134 may operate between about 1 atm and 80 atm, and may have a similar or different pressure than separator 134. Separator 137 may separate the bottoms stream 136 into an overhead stream 138 and a bottoms stream 139. Bottoms stream 139 may comprise butanol and higher boiling components in addition to other reaction products. The bottoms stream 139 may exit the system for use as fuel, as a final product, and/or as a feed to one or more suitable downstream processes. The overhead stream 138 may comprise ethyl acetate as a product stream. In an embodiment, the overhead stream 138 may comprise greater than about 90%, greater than about 95%, greater than about 96%, greater than about 97%, greater than about 98%, greater than about 99%, or greater than about 99.5% ethyl acetate by weight.

The product separation system illustrated in FIG. 11 produces an ethyl acetate product stream 138, a first lights product stream 140, a second lights product stream 131, a third lights product stream 135, a heavies product stream 139, and a recycle stream 141 comprising ethanol. Some portion of the lights streams 131, 135 may be recycled back to the reactive distillation system 129 for use as a hydrogen and/or ethanol feed. While illustrated as a separate feed to the reactive distillation system, the recycle stream 141 may be combined with the feed stream 128 comprising ethanol prior to the combined stream entering the reactive distillation system 129. The embodiment illustrated in FIG. 11 may allow both separator 134 and 137 to operate at similar pressures, which can range from about 1 atm to about 80 atm, from about 5 atm to about 75 atm, from about 10 atm to about 70 atm, or from about 15 atm to about 60 atm.

Dehydrogenation and Dimerization Catalysts

Suitable dehydrogenation and dimerization catalysts are capable of converting at least a portion of the alcohol (e.g., ethanol) in a feed stream to a higher valued product such as ethyl acetate. Any catalyst capable of carrying out a dehydrogenation and dimerization reaction may be used alone or in combination with additional catalytic materials in the reactors. In an embodiment, suitable dehydrogenation and dimerization catalysts can generally comprise metals and/or oxides of copper, barium, ruthenium, rhodium, platinum, palladium, rhenium, silver, cadmium, zinc, zirconium, gold, thallium, magnesium, manganese, aluminum, chromium, nickel, iron, molybdenum, sodium, strontium, tin, and mixtures thereof. In many cases, the catalyst material will be provided on a support material. The catalyst can be treated with a carbonate (e.g., sodium carbonate), reduced with hydrogen, and/or other suitable treatments prior to use.

In certain embodiments, the dehydrogenation and dimerization catalyst may include a catalyst support. The catalyst support stabilizes and supports the catalyst. The type of catalyst support used depends on the chosen catalyst and the reaction conditions. Suitable supports may include, but are not limited to, carbon, silica, silica-alumina, alumina, zirconia, titania, ceria, vanadia, nitride, boron nitride, heteropolyacids, hydroxyapatite, zinc oxide, chromia, zeolites, carbon nanotubes, carbon fullerenes, and any combination thereof.

The dehydrogenation and dimerization catalyst can be employed in any of the conventional types or structures known to the art. It may be employed in the form of extrudates, pills, pellets, granules, broken fragments, or various special shapes. In an embodiment, consideration of the use of the catalyst in the reactive distillation system and/or as a mass transfer surface within the distillation column may be taken into account when determining a suitable shape. For example, the catalyst may have a shape similar to structured packing material or suitable for insertion in a structured packing. When the hydrogenation catalyst is used with one or more side reactors, the catalyst may be disposed within a reaction zone, and the feed may be passed therethrough in the liquid, vapor, or mixed phase, and in either upward or downward, or inward or outward flow.

The dehydrogenation and dimerization catalyst may typically have a range of metal loadings. In an embodiment, the catalyst may have a copper oxide weight loading (i.e., weight percentage) of between about 0.5% and about 80%, between about 10% and about 70%, between about 20% and about 65%, between about 30% and about 60%, or between about 40% and about 50%. In an embodiment, the catalyst may have a zinc oxide weight loading of between about 20% and about 60%, between about 30% and about 50%, or between about 40% and about 50%. In an embodiment, the catalyst may have a chromium oxide weight loading of between about 20% and about 60%, or between about 30% and about 50%.

In an embodiment, the catalyst may comprise $CuO/ZnO/Al_2O_3$. In this embodiment, the catalyst may have a copper oxide weight loading of between about 0.5% and about 80%, between about 10% and about 70%, between about 20% and about 65%, between about 30% and about 60%, or about 40% and about 50%, and the zinc oxide and alumina may comprise the balance of the weight. In an embodiment, the catalyst may comprise $CuO/ZnO/ZrO_2/Al_2O_3$, and the catalyst may have a copper oxide weight loading of between about 40% to about 80%, with the remainder of the components forming the balance of the catalyst weight. In an embodiment, the catalyst may comprise $CuO/ZnO/ZrO_2/Cr_2O_3$, and the catalyst may have a copper oxide weight loading of between about 20% to about 70% and a chromium oxide weight loading between about 30% and about 50%, with the remainder of the components forming the balance of the catalyst weight. In an embodiment, the catalyst comprises an alkaline earth metal and/or alkaline earth metal oxide and copper and/or copper oxide on a support. In this embodiment, the support may comprise silica.

Any of the materials useful as hydrogenation and dimerization catalysts, may be synthesized using a variety of methods. In an embodiment, the dehydrogenation and dimerization catalyst may be prepared via wet impregnation of a catalyst support. Using the wet-impregnation technique, a metal nitrate dissolved in a suitable solvent may be used to prepare the catalyst, however any soluble compound would be suitable. A sufficient amount of solvent should be used to fully dissolve the metal nitrate and appropriately wet the support. In one embodiment, copper nitrate and ethanol and/or water may be mixed in an amount sufficient such that the copper nitrate dissolves. Additional metal nitrates may also be added to provide a catalyst with additional components. The solute may then be combined with a suitable support material of appropriate particle size. The mixture may then be refluxed at a temperature of approximately 100° C. for approximately several hours (e.g., three to five hours) and then allowed to dry at a temperature of about 110° C. The dried material may then be heated to 200° C. to remove the $NO_x$ component, and then the materials may be calcined at about 450° C. to about 550° C. at a heating rate of about one to ten ° C./min. The amount of metal nitrate used in the wet-impregnation technique can be adjusted to achieve a desired final metal weight loading of the catalyst support.

When multiple components are used to provide a catalyst disposed on a support, each component can be added via the wet-impregnation technique. The appropriate salts can be dissolved and impregnated on a support in a co-impregnation process or a sequential process. In a co-impregnation process, measured amount of the appropriate plurality of metal salts may be dissolved in a suitable solvent and used to wet the desired catalyst support. The impregnated support can then be dried and calcined to provide a final catalyst with a desired weight loading. In the sequential impregnation process, one or more measured amounts of salts may be dissolved in a suitable solvent and used to wet the desired catalyst support. The impregnated support can then be dried and calcined. The resulting material can then be wetted with one or more additional salts that are dissolved in a suitable solvent. The resulting material can then be dried and calcined again. This process may be repeated to provide a final catalyst material with a desired loading of each component. In an embodiment, a single metal may be added with each cycle. The order in which the metals are added in the sequential process can be varied. Various metal weight loadings may be achieved through the wet-impregnation technique. In an embodiment, the wet-impregnation technique may be used to provide a catalyst having a copper weight loading ranging from about 0.5% and about 50%, with one or more additional components having a weight loading between about 0.1% and about 10%.

The dehydrogenation and dimerization catalysts may also be prepared via a co-precipitation technique. In this technique, a measured amount of one or more appropriate metal nitrates are dissolved in de-ionized water. The total metal concentration can vary and may generally be between about 1 M and about 3 M. The metal-nitrate solution may then be precipitated through the drop-wise addition of the solution to a stirred, equal volume of a sodium hydroxide solution at room temperature. The sodium hydroxide solution may generally have a concentration of about 4M, though other concentrations may also be used as would be known to one of skill in the art with the benefit of this disclosure. After addition of the metal nitrate solution, the resulting suspension can be filtered and washed with de-ionized water. The filtered solids can be dried overnight, for example, at a temperature of about 110° C. The resulting mixed metal oxide can then be processed to a desired particle size. For example, the resulting mixed metal oxide can be pressed to a desired form, ground, and then sieved to recover a catalyst material with a particle size in a desired range. Catalysts prepared using the co-precipitation technique may have higher metal loadings than the catalysts prepared using the wet-impregnation technique.

The catalyst prepare via the co-precipitation technique may be used in the prepared form and/or a catalyst binder can be added to impart additional mechanical strength. In an embodiment, the prepared catalyst may be ground to a fine powder and then stirred into a colloidal suspension (e.g., a colloidal suspension of silica and/or alumina) in an aqueous solution. The resulting suspension may be stirred while being heated and allowed to evaporate to dryness. The heating may take place at about 80° C. to about 130° C. The resulting solid can then be processed to a desired particle size. For example, the resulting solid can be pressed to a desired form, ground, and then sieved to recover a catalyst material with a particle size in a desired range. Alternatively, the colloidal suspension may be added to the 4M sodium hydroxide precipitation solution prior to addition of the metal nitrate solution in the co-precipitation technique. Various metal weight loadings may be achieved through the co-precipitation technique. In an embodiment, the co-precipitation technique may be used to provide a catalyst having a copper weight loading ranging from about 2% and about 80%, with one or more additional components having a weight loading between about 2% and about 40%.

The resulting catalyst from either the wet-impregnation technique and/or the co-precipitation technique may be further treated prior to use in the reactive distillation system disclosed herein. In an embodiment, the catalyst may be treated with a sodium carbonate solution for a period of time to improve the selectivity of the catalyst. In this process, the catalyst may be soaked in an aqueous solution of sodium carbonate for a period of time ranging from about 1 hour to about 48 hours, or alternatively about 2 hours to about 24 hours. In an embodiment, the sodium carbonate solution may have a concentration of about 0.2 M. The catalyst may then be filtered and allowed to dry at about room temperature. In an embodiment, the sodium carbonate may comprise from about 0.2 to about 3.0 weight percent of the catalyst after being contacted with the sodium carbonate solution.

In another treatment process, the catalyst may be reduced with hydrogen prior to use. In this embodiment, the catalyst may be heated and contacted with hydrogen, which may be flowing over the catalyst, for a period of time sufficient to reduce the catalyst to a desired degree. In an embodiment, the catalyst may be contacted with hydrogen at a temperature of about 190° C. to about 240° C. The hydrogen treatment may be conducted in combination with the sodium carbonate treatment, and may be performed prior to and/or after the sodium carbonate treatment.

Without intending to be limited by theory, it is believed that the production of hydrogen during the dehydrogenation and dimerization reaction within the process may result in contact between the dehydrogenation and dimerization catalyst and a hydrogen stream sufficient to at least partially reduce the catalyst. Thus, the process described herein may have the potential for the in-situ reduction of the catalyst during use. This may result in an initial break-in period in which the catalyst conversion and selectivity may change before reaching a steady state conversion and selectivity. This in-situ reduction may be taken into account when considering the degree to which a catalyst should be pre-reduced with hydrogen.

In an embodiment, the dehydrogenation and dimerization catalyst described herein may be capable of achieving a relatively high conversion and/or selectivity of ethanol to ethyl acetate. As used herein, the "conversion" of ethanol to ethyl acetate refers to the amount of ethanol consumed in the conversion reaction as represented by the formula:

$$X_{ethanol} = 100\left(\frac{F_{EtOH,0} - F_{EtOH}}{F_{EtOH,0}}\right)$$

where $F_{EtOH}$ represents the molar flow rates of ethanol in the reactor effluent (e.g., the product stream comprising the ethyl acetate), and $F_{EtOH,0}$ represents the molar flow rate of ethanol into the reactor inlet. As used herein, the "selectivity" of the conversion refers to the amount of ethanol that is consumed in the conversion reaction that is converted to ethyl acetate as represented by the formula:

$$S = 100\left(\frac{2F_{EtOAC} + F_{AcH}}{F_{EtOH,0} - F_{EtOH}}\right)$$

where $F_{EtOAc}$ and $F_{AcH}$ represent the molar flow rate of ethyl acetate and acetaldehyde in the reactor effluent (e.g., the product stream comprising the ethyl acetate), respectively, and the remaining terms are the same as described above with respect to the conversion of ethanol. In an embodiment, the dehydrogenation and dimerization catalyst described herein may be capable of achieving a conversion of ethanol in the reactive distillation process described herein of at least about 10%, at least about 20%, at least about 30%, at least about 40%, or at least about 50%. In an embodiment, the dehydrogenation and dimerization catalyst described herein may be capable of achieving a selectivity of ethyl acetate in the reactive distillation process described herein of at least about 60%, at least about 70%, at least about 80%, at least about 85%, at least about 90%, or at least about 95%.

Hydrogenation Catalysts

The hydrogenation catalyst generally can include a Group VIII metal and/or a Group VI metal. Examples of such a catalyst can include, but is not limited to, Cu, Re, Ni, Fe, Co, Ru, Pd, Rh, Pt, Os, Ir, and alloys or any combination thereof, either alone or with promoters such as W, Mo, Au, Ag, Cr, Zn, Mn, Sn, B, P, Bi, and alloys or any combination thereof. Other effective hydrogenation catalyst materials include either supported nickel or ruthenium modified with rhenium. In an embodiment, the hydrogenation catalyst also includes any one of the supports described below, depending on the desired functionality of the catalyst. The hydrogenation catalysts may be prepared by methods known to those of ordinary skill in the art.

In an embodiment, the hydrogenation catalyst includes a supported Group VIII metal catalyst and a metal sponge material (e.g., a sponge nickel catalyst). Raney nickel provides an example of an activated sponge nickel catalyst suitable for use in this invention. In an embodiment, the hydrogenation reaction in the invention is performed using a catalyst comprising a nickel-rhenium catalyst or a tungsten-modified nickel catalyst. One example of a suitable catalyst for the hydrogenation reaction of the invention is a carbon-supported nickel-rhenium catalyst.

In an embodiment, a suitable Raney nickel catalyst may be prepared by treating an alloy of approximately equal amounts by weight of nickel and aluminum with an aqueous alkali solution, e.g., containing about 25 weight % of sodium hydroxide. The aluminum is selectively dissolved by the aqueous alkali solution resulting in a sponge shaped material comprising mostly nickel with minor amounts of aluminum. The initial alloy includes promoter metals (e.g., molybdenum or chromium) in the amount such that 1 to 2 weight % remains in the formed sponge nickel catalyst. In another embodiment, the hydrogenation catalyst is prepared using a solution of ruthenium(III) nitrosylnitrate, ruthenium (III) chloride in water to impregnate a suitable support material. The solution is then dried to form a solid having a water content of less than 1% by weight. The solid is then reduced at atmospheric pressure in a hydrogen stream at 300° C. (uncalcined) or 400° C. (calcined) in a rotary ball furnace for 4 hours. After cooling and rendering the catalyst inert with nitrogen, 5% by volume of oxygen in nitrogen is passed over the catalyst for 2 hours.

In certain embodiments, the hydrogenation catalyst may include a catalyst support, which may be the same or different than a catalyst support used with the dehydrogenation and dimerization catalyst. In an embodiment, any of the catalyst supports discussed herein may be used to support a hydrogenation catalyst. The hydrogenation catalyst can be employed in any of the conventional types or structures known to the art. In an embodiment, any of the catalyst shapes and/or types discussed herein with respect to the dehydrogenation and dimerization catalyst may be used with the hydrogenation catalyst.

Production of Methyl Formate from Methanol

In addition to use of the systems and methods described herein for converting ethanol to ethyl acetate, those systems can also be used in processes with methanol as a feed instead of ethanol, with the production of methyl formate and $H_2$ as products according to the following formula:

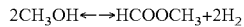

2CH$_3$OH ⇌ HCOOCH$_3$+2H$_2$

Such a system and method can utilize selections from the catalysts indicated for use with the ethanol feed. Products can be withdrawn in similar manner as described for the ethanol to ethyl acetate process.

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

Example 1

Production of Ethyl Acetate from Ethanol

A 10 cm diameter distillation column is used, which has been rendered adiabatic by heating casings with temperatures controlled in such a way that the temperature gradient in the column is reproduced. Over a height of 3.5 m, the column is comprised of rectification zone with 8 stages each with a catalytic cell consisting of a cylindrical container with a flat bottom. The bottom of the container is equipped with a grid for retaining the catalyst and also can act as a gas and liquid distributor. The stripping zone is comprised of 12 stages, also with catalyst-containing cells. The rectification section is considered to be above the feed stage and the stripping section is considered to be below the feed stage. Each catalyst cell contains CuO/ZnO/Al$_2$O$_3$. 200 proof ethanol is fed to the 13$^{th}$ stage of the column, starting from the bottom.

The column is regulated by establishing a reflux ratio which is equal to 0.8, reboil ratio which is equal to 4 and controlling the base temperature to 211° C. and the absolute pressure to 20 bar. The reflux stream is mostly ethanol with small amounts of acetaldehyde. Under stabilized conditions, a bottoms stream and a distillate stream are collected with respective throughputs of about 170 g/h and 4 g/h. The bottoms product gives ethyl acetate purity of 98.5% with small amounts of n-butyraldehyde and butan-2-one.

Example 2

Selective Hydrogenation of n-Butyraldehyde and Butan-2-One

Selective hydrogenation of n-butyraldehyde and butan-2-one in the presence of ethyl acetate was conducted over a hydrogenation catalyst. The reactor was filled with 20 g of 0.1 wt % Pd on silica catalyst. Before the selective hydrogenation reaction, the catalyst was reduced at a temperature of 250° C. for 30 minutes. The catalyst reduction was conducted at atmospheric pressure by delivering hydrogen using a mass flow controller. At the end of this procedure, the catalyst was fully reduced.

The bottoms product from the reactive distillation column, whose composition is given in Table 2, was introduced to a heater at a rate of 30 g/h and mixed with hydrogen prior to admission to the selective hydrogenation reactor. The reaction product was cooled using a jacketed condenser and the liquid condensate was analyzed by gas chromatography. The results are summarized in Table 2, showing n-butyraldehyde and butan-2-one reduced to trace levels.

TABLE 2

Hydrogenation Feed and Products

| Temperature | 250° C. |
| Pressure | 20 atm |

| | Weight % | |
| Component | Feed | Products |
| --- | --- | --- |
| Ethyl acetate | 93 | 92.9 |
| Ethanol | 2 | 2.1 |

TABLE 2-continued

Hydrogenation Feed and Products

| Iso-propanol | 3 | 3 |
|---|---|---|
| n-butyraldehyde | 1.5 | trace |
| butan-2-one | 0.5 | trace |
| 2-butanol | 0 | 0.48 |
| n-butanol | 0 | 1.52 |

Example 3

Wet-Impregnation Catalyst Preparation

Various catalysts including $CuO/SiO_2$, $CuO/SiO_2$—$Al_2O_3$, $CuO/ZnO$, $CuO/ZrO_2$, $CuO/SiO_2$—$ZrO_2$, $CuO/ZnO/Al_2O_3$, $CuO/Cr_2O_3/BaO$, $CuO/Cr_2O_3$ and $CuO/Al_2O_3$ were prepared via impregnation of the corresponding oxide catalyst support. The preparation involved dissolving 4 grams (g) of $Cu(NO_3)_2 \cdot 2.5H_2O$ in 30 mL of de-ionized water, which was then added to 30 g of the appropriate oxide support and stirred until well mixed. The impregnated support was then dried in air at 110° C., followed by calcination in air at 450° C. The amount of $Cu(NO_3)_2 \cdot 2.5H_2O$ was adjusted to achieve a desired final Cu weight loading. Enough water was used to wet the entire oxide support. Copper loadings between 0.5% and 20% by weight were achieved.

Example 4

Co-Impregnation and Sequential Impregnation Catalyst Preparation

Various catalysts including $CuO/ZnO/SiO_2$, $CuO/ZrO_2/SiO_2$, $CuO/MgO/SiO_2$, $CuO/CaO/SiO_2$, $CuO/SrO/SiO_2$, $CuO/BaO/SiO_2$, and $CuO/Na_2O/SiO_2$ were prepared via co-impregnation and sequential impregnation of a silica catalyst support. For the co-impregnation, measured amounts of $Cu(NO_3)_2 \cdot 2.5H_2O$ and $M(NO_3)_x \cdot YH_2O$ (M=Zn, Zr, Mg, Ca, Sr, Ca, or Na; X=1, 2, 4; Y=2-6) were dissolved in de-ionized water. The solution was added to the silica support and stirred until well mixed. The impregnated silica was dried in air at 110° C., followed by calcination in air at 450° C.

For the sequential impregnation, a measured amount of $M(NO_3)_x \cdot YH_2O$ (M=Mg, Ca, Sr, Ca, or Na; X=1 or 2; Y=2-6) was dissolved in de-ionized water. The solution was then added to the silica support and mixed well. The silica was dried at 110° C. and then calcined at 450° C. in air. This procedure was then repeated using $Cu(NO_3)_2 \cdot 2.5H_2O$ in place of the first metal nitrate. Copper loadings between 0.5% and 20% by weight and an addition metal loading between 0.1% and 10% by weight were achieved.

Example 5

Co-Precipitation Catalyst Preparation

Mixed-metal oxide catalysts were prepared via co-precipitation from nitrate solutions. In the co-precipitation synthesis, a measured amount of the appropriate metal nitrate (Cu, Zn, Zr, Al, Cr, Fe, Ni, and/or Ba) were dissolved in de-ionized water (total metal concentration ranges from 1-3 M). The metal-nitrate solution was then precipitated by drop-wise addition to a stirred, equal volume of 4 M aqueous NaOH at room temperature. After addition of all the metal nitrate solution, the suspension was stirred for an additional hour to ensure complete precipitation of the metals. The precipitated solid was then filtered and washed with excess de-ionized water. The solids were then dried overnight at 110° C. The resulting mixed metal oxide was then pressed, ground, and sieved to recover a catalyst with particle sizes between 450 and 850 μm. Catalysts prepared in this manner had copper oxide loadings between 40% and 80% by weight. The loadings of other metal oxides ranged from 2% to 40% by weight. In particular, $CuO/ZnO/ZrO_2/Al_2O_3$, and $CuO/ZnO/ZrO_2/Cr_2O_3$ catalysts were found to be especially active and selective for the dehydrogenative dimerization of ethanol, as illustrated below in Example 6.

In addition to the catalysts prepare above, various catalysts were prepared via co-precipitation and then a binder was incorporated. The catalyst binder was added to the mixed-metal oxide prepared as described above by first grinding the mixed-metal oxide to a fine powder and then stirring it into a colloidal suspension of silica or alumina in water. The resulting suspension was stirred while heating at 80-130° C. to dryness. The resulting solid was then be pressed, ground, and sieved to appropriate particle sizes.

Example 6

Dehydrogenative Dimerization of Ethanol

A portion of the catalysts prepared as described in Examples 3 to 5 were treated with a $Na_2CO_3$ solution by soaking the catalyst in a 0.2 M aqueous solution of $Na_2CO_3$ for 2-24 hrs. The catalyst was then filtered and allowed to dry in air at room temperature. Another portion of the catalysts prepared as described in Examples 3 to 5 were reduced in a hydrogen environment at 175-240° C. for a period of 4-12 hours. These catalysts were then tested in ethanol dehydrogenation reactions. Conversion and selectivity for gas phase reactions were determined from use in a fixed bed reactor operating at 190-240° C. and 1-24 atm. Pure ethanol was fed to the reactor with a weight hourly space velocity (WHSV) between 0.1-1.5 $hr^{-1}$. Conversion and selectivity for liquid phase and mixed liquid/vapor phase reactions were determined in both a fixed bed reactor, operating at 190° C. and at pressures above 25 atm. Liquid phase reactions were also conducted in a batch reactor at 180-200° C. and 20-31 atm (the reactor pressure was maintained above the vapor pressure of ethanol at the operating temperature).

Table 3 shows the conversion and selectivity of the catalysts in a dehydrogenative dimerization reaction conducted in a fixed bed reactor. Conversion (X) and selectivity (S) were calculated from the composition of the reactor effluent as $$X_{ethanol} = 100 \left( \frac{F_{EtOH,0} - F_{EtOH}}{F_{EtOH,0}} \right)$$

$$S = 100 \left( \frac{2F_{EtOAC} + F_{AcH}}{F_{EtOH,0} - F_{EtOH}} \right)$$

Where $F_{EtOH}$, $F_{EtOAc}$, and $F_{AcH}$ represent the molar flow rates of ethanol, ethyl acetate, and acetaldehyde in the reactor effluent, respectively, and $F_{EtOH,0}$ represents the molar flow rate of ethanol into the reactor inlet. Acetaldehyde is a reaction intermediate and so was included in the selectivity calculation.

TABLE 3

Conversion and Selectivity for selected catalysts in a fixed bed reactor at 220° C. and 1 atm

| Catalyst sample | As prepared/received X | As prepared/received S | Reduced in $H_2$ X | Reduced in $H_2$ S |
|---|---|---|---|---|
| Pellet catalysts | | | | |
| $CuO/ZnO/Al_2O_3$ | 18.9 | 92.4 | 35.0 | 89.7 |
| $CuO/Cr_2O_3/BaO$ | 43.5 | 89.4 | 36.0 | 74.6 |
| Impregnated catalysts | | | | |
| $CuO/SiO_2$ | 19.6 | 96.2 | 22.5 | 80.9 |
| $CuO/SiO_2$—$Al_2O_3$ | 43.0 | 17.0 | | |
| $CuO/Al_2O_3$ | 50.2 | 47.3 | | |
| $CuO/ZnO$ | 19.7 | 65.5 | | |
| $CuO/ZrO_2$ | 41.5 | 63.4 | | |
| $CuO/SiO_2$—$ZrO_2$ | 40.0 | 59.7 | | |
| $CuO/MgO/SiO_2$ | 37.9 | 70.0 | 32.1 | 65.7 |
| $CuO/CaO/SiO_2$ | 33.3 | 73.4 | 29.0 | 42.7 |
| $CuO/SrO/SiO_2$ | 25.1 | 77.2 | 31.5 | 69.6 |
| $CuO/BaO/SiO_2$ | 31.0 | 73.2 | 33.6 | 73.6 |
| $CuO/Na_2O/SiO_2$ | 19.4 | 95.9 | | |
| $CuO/ZrO_2/SiO_2$ | 39.1 | 58.7 | 54.0 | 61.6 |
| Co-precipitation catalysts | | | | |
| $CuO/ZnO/ZrO_2/Al_2O_3$ | 8.7 | 83.6 | 21.4 | 72.6 |
| $CuO/ZnO/ZrO_2/Al_2O_3/Na_2CO_3$ | 26.1 | 40.1 | 39.0 | 86.1 |
| $CuO/ZnO/ZrO_2/Cr_2O_3$ | 28.8 | 92.0 | 20.9 | 80.9 |
| $CuO/ZnO/ZrO_2/Cr_2O_3/Na_2CO_3$ | 37.0 | 90.2 | 35.9 | 87.5 |
| $CuO/ZnO/ZrO_2/Fe_2O_3$ | 34.1 | 92.1 | 17.0 | 94.2 |
| $CuO/ZnO/ZrO_2/Fe_2O_3/Na_2CO_3$ | 30.7 | 72.6 | | |
| $CuO/ZnO/ZrO_2/Al_2O_3/Cr_2O_3$ | 24.5 | 88.4 | 18.5 | 79.4 |
| $CuO/ZnO/ZrO_2/Al_2O_3/Cr_2O_3/Na_2CO_3$ | 33.2 | 86.3 | | |

Example 7

Pressure Effects on the Conversion

A fixed bed reactor operated under similar conditions to those described with respect to Example 6 was used to test the reaction conversion and selectivity of a catalyst under varying reaction pressures. Table 4 shows a typical trend in the conversion and selectivity of these catalysts when operated at elevated pressures. Similar trends were seen for all catalysts tested at elevated pressures.

TABLE 4

Conversion and Selectivity for $CuO/ZnO/ZrO_2/Al_2O_3/Na_2CO_3$ (reduced at 240° C. in $H_2$) in a fixed bed reactor at 220° C.

| Pressure (atm) | X | S |
|---|---|---|
| 1 | 39.0 | 86.1 |
| 9.4 | 43.6 | 96.1 |
| 14.5 | 43.3 | 96.4 |
| 21.4 | 39.3 | 97.4 |

As seen by the results in Table 4, operation of catalysts at higher pressures increases the selectivity of the catalyst significantly. Increasing the pressure had little effect on the conversion achieved by the catalysts.

Example 8

Liquid Phase Reaction

The dehydrogenative dimerization of ethanol was also conducted in the liquid phase. Reaction temperatures ranged from 180 to 200° C. and pressures were kept above the vapor pressure of ethanol at the reaction temperature (25-36 atm). Liquid phase reactions were conducted in both a fixed bed reactor and batch reactor. Table 5 shows the results for a $CuO/ZnO/Al_2O_3$ catalyst in a batch reactor operating in the liquid phase. During a typical batch reaction, the pressure initially reached the vapor pressure of ethanol and then slowly increased beyond that pressure as the reaction generated $H_2$ gas. The batch reactor results demonstrated that the dehdrogenative dimerization reaction occurs in the liquid phase.

TABLE 5

Conversion and Selectivity for $CuO/ZnO/Al_2O_3$ (reduced at 240° C. in $H_2$) after 2 hrs in a batch reactor.

| Temperature (° C.) | X | S |
|---|---|---|
| 180 | 4.4 | 84.1 |
| 190 | 6.1 | 81.5 |
| 200 | 13.0 | 96.1 |

Based on the results of Examples 3 through 8, it can be seen that a high selectivity to ethyl acetate using the dehydrogenation and dimerization catalysts described herein (e.g., $CuO/ZnO/ZrO_2/Al_2O_3/Na_2CO_3$ and/or $CuO/ZnO/Al_2O_3$) should enable the use of the system embodiments as illustrated in FIGS. 3, 5 and 7 of the present disclosure. For catalysts where 2-butanone is produced above acceptable levels, the use of the system embodiments as illustrated in FIGS. 4, 6 and 8 of the present disclosure may be used.

Example 9

Effect of Water in the Ethanol Feed

In this example, the effect of water in the ethanol feed was investigated. A 4 wt % water in ethanol solution was fed to a $CuO/ZnO/Al_2O_3$ catalyst in a fixed bed reactor to demonstrate the water tolerance of the catalyst. The reactor was maintained at 21.4 atm and the catalyst was heated to 200-240° C. Table 6 compares the conversion and selectivity achieved for both the 4 wt % water in ethanol and a pure ethanol feed.

TABLE 6

Conversion and selectivity for $CuO/ZnO/Al_2O_3$ in a fixed bed reactor operating at 21.4 atm for ethanol feeds with and without water.

| Temperature (° C.) | Pure Ethanol Feed Conversion | Pure Ethanol Feed Selectivity | 4% Water in Ethanol Feed Conversion | 4% Water in Ethanol Feed Selectivity |
|---|---|---|---|---|
| 200 | 23.2 | 98.1 | 14.2 | 99.2 |
| 220 | 37.9 | 97.1 | 29.2 | 98.6 |
| 240 | 47.9 | 94.4 | 42.6 | 98.0 |

Example 10

Process Simulation of FIG. 10

In an example, a process simulation was performed using the reactive distillation system and product separation system shown in FIG. 10. The simulation was performed using the Aspen Plus V7.1 (Build 23.0.2.4563) software package. The physical properties are provided in degrees Celsius (° C.), psig, pounds per hour (lb/hr), U.S. gallons per minute (US- GPM), and British thermal units per hour (Btu/hr). The material streams, their compositions, and the associated unit properties produced by the simulation are provided in Tables 7, 8, and 9 below, respectively.

TABLE 7A

Material Streams

| Name | Feed Stream 111 | Recycle Stream 127 |
|---|---|---|
| Vapor Fraction | 0 | 0 |
| Temperature (° C.) | 50 | 169 |
| Pressure (psig) | 294 | 382 |
| Molar Flow (lbmol/h) | 502.4 | 877.9 |
| Mass Flow (lb/hr) | 23142 | 43511.5 |
| Liquid Volume Flow (USGPM) | 60.1 | 143.6 |
| Heat Flow (Btu/hr) | −5.92E7 | −1.01E8 |

TABLE 7B

Material Streams

| Name | Liquid Stream 116 | Bottoms Stream 119 | Vapor Overhead Stream 121 |
|---|---|---|---|
| Vapor Fraction | 0 | 0 | 1 |
| Temperature (° C.) | −10 | 88.3 | 74.4 |
| Pressure (psig) | 274.8 | 352.7 | 10 |
| Molar Flow (lbmol/h) | 1141 | 892 | 12.6 |
| Mass Flow (lb/hr) | 65659 | 44260 | 630.8 |
| Liquid Volume Flow (USGPM) | 148.9 | 120.2 | — |
| Heat Flow (Btu/hr) | −1.65E8 | −1.09E8 | −1.3E6 |

TABLE 7C

Material Streams

| Name | Overhead Stream 123 | Bottoms Stream 124 | Heavies Product Stream 126 |
|---|---|---|---|
| Vapor Fraction | 0 | 0 | 0 |
| Temperature (° C.) | 175 | 208 | 224 |
| Pressure (psig) | 279 | 285 | 338 |
| Molar Flow (lbmol/h) | 1016 | 236 | 7.4 |
| Mass Flow (lb/hr) | 54267 | 20756 | 581 |
| Liquid Volume Flow (USGPM) | 180.2 | 69.6 | 0.3 |
| Heat Flow (Btu/hr) | −1.2E8 | −4.4E7 | −1.05E6 |

TABLE 8A

Stream Compositions

| Name | Feed Stream 111 | Recycle Stream 127 |
|---|---|---|
| Comp Mole Frac (Ethanol) | 1 | 0.87 |
| Comp Mole Frac (Ethyl Acetate) | 0 | 0.13 |
| Comp Mole Frac (Hydrogen) | 0 | 0 |
| Comp Mole Frac (Butanol) | 0 | 0 |
| Comp Mole Frac (n-butyraldehyde) | 0 | 0 |
| Comp Mole Frac (butan-2-one) | 0 | 0 |

TABLE 8B

Stream Compositions

| Name | Liquid Stream 116 | Bottoms Stream 119 | Vapor Overhead Stream 121 |
|---|---|---|---|
| Comp Mole Frac (Ethanol) | 0.69 | 0.85 | 0.39 |
| Comp Mole Frac (Ethyl Acetate) | 0.29 | 0.13 | 0.32 |
| Comp Mole Frac (Hydrogen) | 0 | 0 | 0.13 |
| Comp Mole Frac (Butanol) | 0 | 0 | 0 |
| Comp Mole Frac (n-butyraldehyde) | 0 | 0 | 0 |
| Comp Mole Frac (butan-2-one) | 0 | 0 | 0 |

TABLE 8C

Stream Compositions

| Name | Overhead Stream 123 | Bottoms Stream 124 | Heavies Product Stream 126 |
|---|---|---|---|
| Comp Mole Frac (Ethanol) | 0.61 | 0 | 0.01 |
| Comp Mole Frac (Ethyl Acetate) | 0.29 | 99.8 | 0.57 |
| Comp Mole Frac (Hydrogen) | 0 | 0 | 0 |
| Comp Mole Frac (Butanol) | 0 | 0.1 | 0.40 |
| Comp Mole Frac (n-butyraldehyde) | 0 | 0 | 0 |
| Comp Mole Frac (butan-2-one) | 0 | 0.1 | 0 |

TABLE 9

Unit Properties

| Name | Separator 120 | Separator 122 | Separator 125 |
|---|---|---|---|
| Pressure (psig) | 10 | 279 | 338 |
| Theoretical Stages | 30 | 20 | 32 |
| Condenser Duty (Btu/hr) | −3.3E7 | −2.5E7 | −2.3E7 |
| Reboiler Duty (Btu/hr) | 2.2E7 | 3.6E7 | 2.9E7 |

Example 11

Process Simulation of FIG. 11

As another example, a similar process simulation was performed using the reactive distillation system and product separation system shown in FIG. 11. The material streams, their compositions, and the associated unit properties produced by the simulation are provided in Tables 10, 11, and 12 below, respectively.

TABLE 10A

Material Streams

| Name | Feed Stream 128 | Recycle Stream 141 |
|---|---|---|
| Vapor Fraction | 0 | 0 |
| Temperature (° C.) | 50 | 168 |
| Pressure (psig) | 294 | 382 |
| Molar Flow (lbmol/h) | 502.4 | 893 |
| Mass Flow (lb/hr) | 23148 | 44429 |
| Liquid Volume Flow (USGPM) | 60 | 146 |
| Heat Flow (Btu/hr) | −5.9E7 | −1E8 |

TABLE 10B

Material Streams

| Name | Liquid Stream 132 | Vapor Overhead Stream 135 | Bottoms Stream 136 |
|---|---|---|---|
| Vapor Fraction | 0 | 1 | 0 |
| Temperature (° C.) | −10 | 125 | 205 |
| Pressure (psig) | 275 | 265 | 270 |
| Molar Flow (lbmol/h) | 1155 | 1.76 | 250 |
| Mass Flow (lb/hr) | 66568 | 26.2 | 21894 |
| Liquid Volume Flow (USGPM) | 150.8 | 6 | 72.6 |
| Heat Flow (Btu/hr) | −1.6E8 | −48670 | −4.6E7 |

TABLE 10C

Material Streams

| Name | Overhead Stream 138 | Bottoms Stream 139 |
|---|---|---|
| Vapor Fraction | 0 | 0 |
| Temperature (° C.) | 202 | 210 |
| Pressure (psig) | 250 | 260 |
| Molar Flow (lbmol/h) | 240 | 9.7 |
| Mass Flow (lb/hr) | 21101 | 792 |
| Liquid Volume Flow (USGPM) | 68 | 2.6 |
| Heat Flow (Btu/hr) | −4.5E7 | −1.5E6 |

TABLE 11A

Stream Compositions

| Name | Feed Stream 128 | Recycle Stream 141 |
|---|---|---|
| Comp Mole Frac (Ethanol) | 1.0 | 0.91 |
| Comp Mole Frac (Ethyl Acetate) | 0 | 0.09 |
| Comp Mole Frac (Hydrogen) | 0 | 0 |
| Comp Mole Frac (Butanol) | 0 | 0 |
| Comp Mole Frac (n-butyraldehyde) | 0 | 0 |
| Comp Mole Frac (butan-2-one) | 0 | 0 |

TABLE 11B

Stream Compositions

| Name | Liquid Stream 132 | Vapor Overhead Stream 135 | Bottoms Stream 136 |
|---|---|---|---|
| Comp Mole Frac (Ethanol) | 0.70 | 0.23 | 0 |
| Comp Mole Frac (Ethyl Acetate) | 0.27 | 0.03 | 0.97 |
| Comp Mole Frac (Hydrogen) | 0 | 0.73 | 0 |
| Comp Mole Frac (Butanol) | 0.01 | 0 | 0 |
| Comp Mole Frac (n-butyraldehyde) | 0 | 0 | 0.02 |
| Comp Mole Frac (butan-2-one) | 0 | 0 | 0 |

TABLE 11C

Stream Compositions

| Name | Overhead Stream 138 | Bottoms Stream 139 |
|---|---|---|
| Comp Mole Frac (Ethanol) | 0 | 0 |
| Comp Mole Frac (Ethyl Acetate) | 0.99 | 0.57 |
| Comp Mole Frac (Hydrogen) | 0 | 0 |
| Comp Mole Frac (Butanol) | 0 | 0.40 |
| Comp Mole Frac (n-butyraldehyde) | 0 | 0 |
| Comp Mole Frac (butan-2-one) | 0.01 | 0 |

TABLE 12

Unit Properties

| Name | Separator 133 | Separator 134 | Separator 137 |
|---|---|---|---|
| Pressure (psig) | 274.8 | 264.5 | 250 |
| Theoretical Stages | 1 | 40 | 32 |
| Condenser Duty (Btu/hr) | −5.6E6 | −4E7 | −2.2E7 |
| Reboiler Duty (Btu/hr) | — | 4.6E7 | 2.2E7 |

In the preceding discussion and in the claims, the terms "including" and "comprising" are used in an open-ended fashion, and thus should be interpreted to mean "including, but not limited to . . . ". At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, Rl, and an upper limit, Ru, is disclosed, any number falling within the range is specifically disclosed. In particular, the following numbers within the range are specifically disclosed: R=Rl+k*(Ru−Rl), wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present invention.

What is claimed is:

1. A reactive distillation method comprising:
introducing a feed stream to a reactive distillation column, wherein the feed stream comprises ethanol;

contacting the feed stream with a catalyst in the reactive distillation column during a distillation, wherein the feed stream reacts in the presence of the catalyst to produce a reaction product comprising ethyl acetate and hydrogen, wherein the catalyst comprises copper or copper oxide, wherein the catalyst has a copper weight loading of greater than about 10%, and wherein the catalyst has a copper weight loading of less than about 80% of the catalyst;

removing ethyl acetate during the distillation from the reactive distillation column as a bottoms stream, wherein the selective of the conversion of the ethanol in the feed stream to the ethyl acetate in the bottom stream is at least about 60%; and removing hydrogen during the distillation from the reactive distillation column as an overhead stream.

2. The reactive distillation method of claim 1, further comprising:
contacting the bottoms stream with a hydrogenation catalyst and hydrogen to hydrogenate at least a portion of a contaminant in the bottoms stream; and
separating the hydrogenated portion of the contaminant from the bottoms stream.

3. The reactive distillation method of claim 2, wherein the hydrogenation catalyst comprises a Group VIII metal, a Group VI metal, or any combination thereof.

4. The reactive distillation method of claim 1, wherein the catalyst further comprises at least one catalytic component selected from the group consisting of: barium, barium oxide, ruthenium, ruthenium oxide, rhodium, rhodium oxide, platinum, platinum oxide, palladium, palladium oxide, rhenium, rhenium oxide, silver, silver oxide, cadmium, cadmium oxide, zinc, zinc oxide, zirconium, zirconium oxide, gold, gold oxide, thallium, thallium oxide, magnesium, magnesium oxide, manganese, manganese oxide, aluminum, aluminum oxide, chromium, chromium oxide, nickel, nickel oxide, iron, iron oxide, molybdenum, molybdenum oxide, sodium, sodium oxide, sodium carbonate, strontium, strontium oxide, tin, tin oxide, and any mixture thereof.

5. The reactive distillation method of claim 1, wherein the catalyst comprises a support, wherein the support comprises at least one support material selected from the group consisting of: carbon, silica, silica-alumina, alumina, zirconia, titania, ceria, vanadia, nitride, boron nitride, heteropolyacids, hydroxyapatite, zinc oxide, chromia, a zeolite, a carbon nanotube, carbon fullerene, and any combination thereof.

6. The reactive distillation method of claim 1, wherein the catalyst comprises copper oxide and zinc oxide disposed on a support.

7. The reactive distillation method of claim 1, wherein. the catalyst comprises copper oxide, zinc oxide, zirconium oxide, and alumina.

8. The reactive distillation method of claim 1, wherein the catalyst comprises copper oxide, zinc oxide, zirconium oxide, and chromium oxide.

9. The reactive distillation method of claim 1, wherein the catalyst comprises:
an alkaline earth metal or alkaline earth metal oxide,
copper or copper oxide, and
a support.

10. The reactive distillation method of claim 1, wherein the catalyst comprises sodium carbonate.

11. The reactive distillation method of claim 1, wherein the catalyst is at least partially reduced in the presence of hydrogen.

12. The reactive distillation method of claim 1, wherein a conversion of ethanol in the feed stream is at least about 10%.

13. The reactive distillation method of claim 1, further comprising:
removing a side stream from the reactive distillation column, and
contacting the side stream with a second catalyst, wherein the side stream reacts in the presence of the second catalyst to produce ethyl acetate, 14. The reactive distillation method of claim 1, wherein a liquid portion of the feed stream reacts in the presence of the catalyst to produce a reaction product comprising ethyl acetate and hydrogen.

15. A reactive distillation method comprising:
introducing a feed stream to a reactive distillation column, wherein the feed stream comprises ethanol;
contacting the feed stream with a catalyst in the reactive distillation column during a distillation, wherein the feed stream reacts in the presence of the catalyst to produce a reaction product comprising ethyl acetate and hydrogen;
separating a bottoms stream during the distillation from the reactive distillation column, wherein the bottoms stream comprises ethyl acetate and ethanol, wherein the selectivity of the conversion of the ethanol in the feed stream to the ethyl acetate in the bottom stream is at least about 60%;
separating a recycle stream from the bottoms stream, wherein separating the recycle stream from the bottoms stream comprises:
separating the bottoms stream into a product stream and the recycle stream,
wherein the recycle stream comprises at least a portion of the ethanol from the bottoms stream; and
recycling the recycle stream to the reactive distillation column.

16. The reactive distillation of claim 15,
wherein the product stream comprises byproducts an ethyl acetate; and wherein the method further comprises:
separating the product stream into a byproducts stream and an ethyl acetate product stream.

17. The reactive distillation method of claim 16, further comprises;
combining the byproducts stream with the bottoms stream in the separation of the bottoms stream into the product stream and the recycle stream.

18. The reactive distillation method of claim 15, further comprising;
separating at least one byproduct from the recycle stream after separation of the recycle stream from the bottoms stream and prior to recycling the recycle stream to the reactive distillation column.

19. A reactive distillation process comprising:
introducing a feed stream to a reactive distillation column during a distillation, wherein the feed stream comprises ethanol;
drawing a first fluid from the reactive distillation column during the distillation, wherein the first fluid comprises ethanol;
contacting the first fluid with a dehydrogenation catalyst in a side reactor, wherein the dehydrogenation catalyst comprises copper or copper oxide, wherein the dehydrogenation catalyst has a copper weight loading of greater than about 10%, and wherein the dehydrogenation catalyst has a copper weight loading of less than about 80% of the catalyst;
producing a reaction product comprising ethyl acetate in response to contacting the first fluid with the dehydrogenation catalyst in the side reactor;

introducing the ethyl acetate to the reactive distillation column from the side reactor during the distillation;

removing ethyl acetate during the distillation from the reactive distillation column as a bottoms stream, wherein the selective of the conversion at the ethanol in the feed stream to the ethyl acetate n the bottoms stream is at least about 60%; and removing hydrogen during the distillation from the reactive distillation column as an overhead stream.

20. The reactive distillation process of claim 19, wherein at least one of the reactive distillation column or the side reactor comprises a hydrogenation catalyst.

21. The reactive distillation process of claim 20, wherein the reactive distillation column comprises the hydrogenation catalyst, and further comprising:

introducing a second feed stream to the reactive distillation column, wherein the second feed stream comprises hydrogen; and contacting the hydrogen with the hydrogenation catalyst during the reactive distillation process.

22. The reactive distillation process of claim 20, wherein producing a reactive product comprising ethyl acetate further produces by-products, and wherein the reactive distillation process farther comprises:

hydrogenating at least a portion of the by-products over the hydrogenation. catalyst to prodnce hydrogenated by-products.

23. The reactive distillation process of claim 19, further comprising:

contacting a second fluid drawn from the reactive, distillation column with a second catalyst in a second side reactor.

24. The reactive distillation process of claim 23, wherein the second catalyst comprises a second dehydrogenation catalyst.

25. The reactive distillation process of claim 24, wherein the dehydrogenation catalyst and the second dehydrogenation catalyst comprise the same components.

26. The reactive distillation process of claim 24, wherein the dehydrogenation catalyst and the second dehydrogenation catalyst comprise different components.

27. The reactive distillation process of claim 24, wherein the side reactor and the second side reactor each provide a different catalyst holdup.

28. The reactive distillation process of claim 23, wherein the second catalyst comprises a hydrogenation catalyst.

29. The reactive distillation method of claim 1. wherein the reactive distillation column further comprises a hydrogenation catalyst, and wherein the method further comprises: contacting the reaction product with the hydrogenation catalyst within the reactive distillation column.

30. The reactive distillation method of claim 1, wherein the catalyst comprises copper oxide, zircoinum oxide, and alumina.

31. The reactive distillation method of claim 1, wherein the catalyst further comprises at least one of zirconium or zirconium oxide.

32. The reactive distillation method of claim 1, wherein the catalyst further comprises at least one of aluminum or aluminum oxide.

33. The reactive distillation method of claim 1, wherein the catalyst further comprises silica.

34. The reactive distillation method of claim 1, wherein the catalyst further comprises: silica, a metal or oxide of zirconium, and a metal or oxide of aluminum.

35. The reactive distillation method of claim 16, wherein separating the bottoms stream into the product stream and the recycle stream comprises separating the bottoms stream into the product stream and the recycle stream at a first pressure; and wherein separating the product stream into the byproduct stream and the ethyl acetate product stream comprises separating the product stream into the byproduct stream and the ethyl acetate product stream at a second pressure, wherein the second pressure is greater than the first pressure.

36. The reactive distillation method of claim 19, wherein the catalyst further comprises at least one of zirconium or zirconium oxide.

37. The reactive distillation method of claim 19, wherein the catalyst further comprises at least one of aluminum or aluminum oxide, 38. The reactive distillation method of claim 19, wherein the catalyst further comprises silica.

* * * * *

UNITED STATES PATENT AND TRADEMARK OFFICE
CERTIFICATE OF CORRECTION

PATENT NO. : 9,079,851 B2
APPLICATION NO. : 13/363858
DATED : July 14, 2015
INVENTOR(S) : Sagar B. Gadewar et al.

It is certified that error appears in the above-identified patent and that said Letters Patent is hereby corrected as shown below:

In the specification

Col. 27, Lines 7-21, replace Table 7A,

" [illegible original Table 7A image] "

with

TABLE 7A
Material Streams

| Name | Feed Stream 111 | Recycle Stream 127 |
|---|---|---|
| Vapor Fraction | 0 | 0 |
| Temperature (°C) | 50 | 169 |
| Pressure (psig) | 294 | 382 |
| Molar Flow (lbmol/h) | 502.4 | 877.9 |
| Mass Flow (lb/hr) | 23142 | 43511.5 |
| Liquid Volume Flow (USGPM) | 60.1 | 143.6 |
| Heat Flow (Btu/hr) | -5.92E7 | -1.01E8 |

--                                                                              --

In the claims

In Claim 1, col. 31, line 12 replace "selective" with --selectivity--

Signed and Sealed this
Fifteenth Day of December, 2015

Michelle K. Lee
*Director of the United States Patent and Trademark Office*

CERTIFICATE OF CORRECTION (continued)
U.S. Pat. No. 9,079,851 B2

In Claim 1, col. 31, line 13 replace "bottom" with --bottoms--

In Claim 16, col. 32, line 36 replace "an" with --and--

In Claim 17, col. 32, line 41 replace "comprise" with --comprising--

In Claim 19, col. 33, line 5 replace "selective" with --selectivity--

In Claim 19, col. 33, line 5 replace "at" with --of--

In Claim 19, col. 33, line 8 replace "n" with --in--

In Claim 22, col. 33, line 25 replace "farther" with --further--

In Claim 22, col. 33, line 27 replace "hydrogenation." with --hydrogenation--

In Claim 23, col. 33, line 31 replace "reactive." with --reactive--

In Claim 30, col. 34, line 12 replace "zircoinum" with --zirconium--

In Claim 37, col. 34, line 38 replace "oxide," with --oxide.--